United States Patent
Fujita et al.

(10) Patent No.: US 11,492,410 B2
(45) Date of Patent: Nov. 8, 2022

(54) METHOD FOR TREATING CANCER BY ADMINISTRATION OF ANTIBODIES THAT BIND TO EXTRACELLULAR REGION PORTION OF MCEMP1 PROTEIN

(71) Applicant: TORAY INDUSTRIES, INC., Tokyo (JP)

(72) Inventors: Takayuki Fujita, Kamakura (JP); Fumiyoshi Okano, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/088,502

(22) PCT Filed: Mar. 27, 2017

(86) PCT No.: PCT/JP2017/012239
§ 371 (c)(1),
(2) Date: Sep. 26, 2018

(87) PCT Pub. No.: WO2017/170322
PCT Pub. Date: Oct. 5, 2017

(65) Prior Publication Data
US 2019/0106505 A1    Apr. 11, 2019

(30) Foreign Application Priority Data
Mar. 28, 2016 (JP) .............................. JP2016-064035

(51) Int. Cl.
| | | |
|---|---|---|
| A61K 47/68 | (2017.01) | |
| A61K 39/395 | (2006.01) | |
| C07K 16/30 | (2006.01) | |
| A61K 45/00 | (2006.01) | |
| A61K 38/00 | (2006.01) | |
| C07K 16/28 | (2006.01) | |
| A61P 35/00 | (2006.01) | |
| A61K 45/06 | (2006.01) | |
| A61K 39/00 | (2006.01) | |
| C12N 15/09 | (2006.01) | |

(52) U.S. Cl.
CPC .............. *C07K 16/30* (2013.01); *A61K 38/00* (2013.01); *A61K 39/39558* (2013.01); *A61K 45/00* (2013.01); *A61K 45/06* (2013.01); *A61P 35/00* (2018.01); *C07K 16/28* (2013.01); *A61K 2039/505* (2013.01); *C07K 2317/732* (2013.01); *C12N 15/09* (2013.01)

(58) Field of Classification Search
CPC combination set(s) only.
See application file for complete search history.

(56) References Cited

U.S. PATENT DOCUMENTS

2005/0288487 A1    12/2005    Li et al.

FOREIGN PATENT DOCUMENTS

| JP | 2003-513610 A | 4/2003 |
|---|---|---|
| JP | 2005-528087 A | 9/2005 |
| KR | 10-2010-0121949 A | 11/2010 |
| WO | WO 00/55180 | * 9/2000 |
| WO | WO 00/55180 A2 | 9/2000 |
| WO | WO 03/057252 | * 7/2003 |
| WO | WO 03/057252 A | 7/2003 |
| WO | WO 03/057252 A1 | 7/2003 |
| WO | WO 2011/144718 A2 | 11/2011 |

OTHER PUBLICATIONS

Li et al (Genomics, 2005, 86:68-75).*
He et al (PNAS, 2016, 113:11931-11936).*
Weitzman et al (Leukemia & Lymphoma, 2009, 50:1361-1368).*
International Search Report, issued in PCT/JP2017/012239, dated May 9, 2017.
Written Opinion of the international Searching Authority, issed in PCT/JP2017/012239, dated May 9, 2017.
Database WPI Week 281152,Thomson Scientific, London, GB; AN 2810-Q33578, XP02794675, & KR 2010 0121949 A (Korea Res Inst Bioscience & Biotechnology) Nov. 19, 2010 (Nov. 19, 2010) * abstract *.
Extended European Search Report dated Oct. 11, 2019, in European Patent Application No. 17774859.7.
Li et al., "Identification and expression of a new type II transmembrane protein in human mast cells," Genomics (2005), vol. 86, pp. 68-75.
Database WPI Week 201152,Thomson Scientific, London, GB; AN 2010-Q33578, XP002794675, & KR 2010 0121949 A(Korea Res Inst Bioscience & Biotechnology) Nov. 19, 2010 (Nov. 19, 2010) * abstract *.

* cited by examiner

*Primary Examiner* — Laura B Goddard
(74) *Attorney, Agent, or Firm* — Birch, Stewart, Kolasch & Birch, LLP

(57) ABSTRACT

An object of the present invention is to identify cancer antigen proteins specifically expressed on the surface of cancer cells and to provide a use of antibodies targeting such proteins as therapeutic and/or preventive agents for cancer. The present invention relates to, for example, a pharmaceutical composition for treatment and/or prevention of a cancer, which comprises, as an active ingredient, an antibody or fragment thereof having an immunological reactivity with an MCEMP1 protein having an amino acid sequence shown in any one of the even numbered SEQ ID NOS: 2 to 8 or an amino acid sequence having 80% or more sequence identity with the amino acid sequence, or with a fragment of the MCEMP1 protein comprising 7 or more consecutive amino acids.

8 Claims, 4 Drawing Sheets

Specification includes a Sequence Listing.

SEQUENCE LISTING

```
<160> NUMBER OF SEQ ID NOS: 30

<210> SEQ ID NO 1
<211> LENGTH: 1326
<212> TYPE: DNA
<213> ORGANISM: Homo sapiens
<220> FEATURE:
<221> NAME/KEY: CDS
```

<222> LOCATION: (26)..(589)

<400> SEQUENCE: 1

| | | |
|---|---|---|
| tggacaaatt tgcgggctgg ggacc atg gaa gtg gag gaa atc tac aag cac | | 52 |
| Met Glu Val Glu Glu Ile Tyr Lys His | | |
| 1 5 | | |
| cag gaa gtc aag atg caa gca cca gcc ttc agg gac aag aaa cag ggg | | 100 |
| Gln Glu Val Lys Met Gln Ala Pro Ala Phe Arg Asp Lys Lys Gln Gly | | |
| 10 15 20 25 | | |
| gtc tca gcc aag aat caa ggt gcc cat gac cca gac tat gag aat atc | | 148 |
| Val Ser Ala Lys Asn Gln Gly Ala His Asp Pro Asp Tyr Glu Asn Ile | | |
| 30 35 40 | | |
| acc ttg gcc ttc aaa aat cag gac cat gca aag ggt ggt cat tca cga | | 196 |
| Thr Leu Ala Phe Lys Asn Gln Asp His Ala Lys Gly Gly His Ser Arg | | |
| 45 50 55 | | |
| ccc acg agc caa gtc cca gcc cag tgc agg ccg ccc tca gac tcc acc | | 244 |
| Pro Thr Ser Gln Val Pro Ala Gln Cys Arg Pro Pro Ser Asp Ser Thr | | |
| 60 65 70 | | |
| cag gtc ccc tgc tgg ttg tac aga gcc atc ctg agc ctg tac atc ctc | | 292 |
| Gln Val Pro Cys Trp Leu Tyr Arg Ala Ile Leu Ser Leu Tyr Ile Leu | | |
| 75 80 85 | | |
| ctg gcc ctg gcc ttt gtc ctc tgc atc atc ctg tca gcc ttc atc atg | | 340 |
| Leu Ala Leu Ala Phe Val Leu Cys Ile Ile Leu Ser Ala Phe Ile Met | | |
| 90 95 100 105 | | |
| gtg aag aat gct gag atg tcc aag gag ctg ctg ggc ttt aaa agg gag | | 388 |
| Val Lys Asn Ala Glu Met Ser Lys Glu Leu Leu Gly Phe Lys Arg Glu | | |
| 110 115 120 | | |
| ctt tgg aat gtc tca aac tcc gta caa gca tgc gaa gag aga cag aag | | 436 |
| Leu Trp Asn Val Ser Asn Ser Val Gln Ala Cys Glu Glu Arg Gln Lys | | |
| 125 130 135 | | |
| aga ggc tgg gat tcc gtt cag cag agc atc acc atg gtc agg agc aag | | 484 |
| Arg Gly Trp Asp Ser Val Gln Gln Ser Ile Thr Met Val Arg Ser Lys | | |
| 140 145 150 | | |
| att gat aga tta gag acg aca tta gca ggc ata aaa aac att gac aca | | 532 |
| Ile Asp Arg Leu Glu Thr Thr Leu Ala Gly Ile Lys Asn Ile Asp Thr | | |
| 155 160 165 | | |
| aag gta cag aaa atc ttg gag gtg ctg cag aaa atg cca cag tcc tca | | 580 |
| Lys Val Gln Lys Ile Leu Glu Val Leu Gln Lys Met Pro Gln Ser Ser | | |
| 170 175 180 185 | | |
| cct caa taa atgagaggac attgtggcag ccaaagccac aacttggaag | | 629 |
| Pro Gln | | |
| atggggctgc acctgccaac gaagacggga atgacccccc cccccccagc ctagtgtgaa | | 689 |
| cctgccctc gtcccacgta tagaaaaacc tcgagtcatg gtgaatgagt gtctcggagt | | 749 |
| tgctcgtgtg tgtgtacacc tgcgtgcgtg tgtgtgcgtg tgtgcgcgtg tgttcgtgta | | 809 |
| tgtgcgtgtg tgcgtgcgcg tgtgtgtgca ttttgcaaag ggtggacatt tcagtgtatc | | 869 |
| tcccagaaag gtgatgaatg aataggactg agagtcacag tgaatgtggc atgcatgcct | | 929 |
| gtgtcatgtg acatatgtga gtctcggcat gtcacggtgg gtggctgtgt ctgagcacct | | 989 |
| ccagcagatg tcactctgag tgtgggtgtt ggtgacatgc attgcacggg cctgtctccc | | 1049 |
| tgtttgtgta aacatactag agtatactgc ggcgtgtttt ctgtctaccc atgtcatggt | | 1109 |
| gggggagatt tatctccgta catgtgggtg tcgccatgtg tgccctgtca ctatctgtgg | | 1169 |
| ctgggtgaac ggctgtgtca ttatgagtgt gccgagttat gccaccctgt gtgctcaggg | | 1229 |
| cacatgcaca cagacattta tctctgcact cacattttgt gacttatgaa gataaataaa | | 1289 |
| gtcaagggaa aacagcgtca aaaaaaaaaa aaaaaaa | | 1326 |

<210> SEQ ID NO 2
<211> LENGTH: 187
<212> TYPE: PRT
<213> ORGANISM: Homo sapiens

<400> SEQUENCE: 2

```
Met Glu Val Glu Glu Ile Tyr Lys His Gln Glu Val Lys Met Gln Ala
1               5                   10                  15

Pro Ala Phe Arg Asp Lys Lys Gln Gly Val Ser Ala Lys Asn Gln Gly
            20                  25                  30

Ala His Asp Pro Asp Tyr Glu Asn Ile Thr Leu Ala Phe Lys Asn Gln
        35                  40                  45

Asp His Ala Lys Gly Gly His Ser Arg Pro Thr Ser Gln Val Pro Ala
    50                  55                  60

Gln Cys Arg Pro Pro Ser Asp Ser Thr Gln Val Pro Cys Trp Leu Tyr
65                  70                  75                  80

Arg Ala Ile Leu Ser Leu Tyr Ile Leu Leu Ala Leu Ala Phe Val Leu
                85                  90                  95

Cys Ile Ile Leu Ser Ala Phe Ile Met Val Lys Asn Ala Glu Met Ser
            100                 105                 110

Lys Glu Leu Leu Gly Phe Lys Arg Glu Leu Trp Asn Val Ser Asn Ser
        115                 120                 125

Val Gln Ala Cys Glu Glu Arg Gln Lys Arg Gly Trp Asp Ser Val Gln
    130                 135                 140

Gln Ser Ile Thr Met Val Arg Ser Lys Ile Asp Arg Leu Glu Thr Thr
145                 150                 155                 160

Leu Ala Gly Ile Lys Asn Ile Asp Thr Lys Val Gln Lys Ile Leu Glu
                165                 170                 175

Val Leu Gln Lys Met Pro Gln Ser Ser Pro Gln
            180                 185
```

<210> SEQ ID NO 3
<211> LENGTH: 1124
<212> TYPE: DNA
<213> ORGANISM: Canis familiaris
<220> FEATURE:
<221> NAME/KEY: CDS
<222> LOCATION: (66)..(689)

<400> SEQUENCE: 3

```
ctcatctgcc atgacacctt ccggtgggtg gggatgtgtg tgggtaaact ggcccactgg     60 gaacc atg gag tct gag gaa atc tac acg aat cag aag gtc gag atg cag    110
      Met Glu Ser Glu Glu Ile Tyr Thr Asn Gln Lys Val Glu Met Gln
      1               5                   10                  15 gca gcc ttc aaa gac aag aaa cag agg gtc cca gct gat aag gaa ggt     158
Ala Ala Phe Lys Asp Lys Lys Gln Arg Val Pro Ala Asp Lys Glu Gly
                20                  25                  30 gca gat aac cct gac tat gag aat atc acc ttg gcc ttc aga aac cag     206
Ala Asp Asn Pro Asp Tyr Glu Asn Ile Thr Leu Ala Phe Arg Asn Gln
            35                  40                  45 gac cag cca aag ggc agc cat tta cca ccc aag aat cag agc aag cag     254
Asp Gln Pro Lys Gly Ser His Leu Pro Pro Lys Asn Gln Ser Lys Gln
        50                  55                  60 cca cct gcc agg aca cat cac acg gcc ttg gga ggg gcc cac gtc cca     302
Pro Pro Ala Arg Thr His His Thr Ala Leu Gly Gly Ala His Val Pro
65                  70                  75 acc ctg tct agg ctg ccc tca gac tct ggc cag ctc ccc cgt tgt ctg     350
Thr Leu Ser Arg Leu Pro Ser Asp Ser Gly Gln Leu Pro Arg Cys Leu
```

```
                80                  85                  90                  95
cac aga gtc atc atg agc ctg tac atg ctc ctc gcc ctg tcc tgc atc               398
His Arg Val Ile Met Ser Leu Tyr Met Leu Leu Ala Leu Ser Cys Ile
                    100                 105                 110 att ctc tta gtc ttg gtc ctc atg aag aat ctg gag atg tcc cag gag               446
Ile Leu Leu Val Leu Val Leu Met Lys Asn Leu Glu Met Ser Gln Glu
            115                 120                 125 ttg ctg gcc ctg aaa agg gag ctc tgg aat gtg tcc gtc tcg gtg caa               494
Leu Leu Ala Leu Lys Arg Glu Leu Trp Asn Val Ser Val Ser Val Gln
        130                 135                 140 gag tgc cag gag cag cag aat cag ggc tgg agc acc gtc cgg cag ctc               542
Glu Cys Gln Glu Gln Gln Asn Gln Gly Trp Ser Thr Val Arg Gln Leu
    145                 150                 155 ctg gtg gag gcc aag cgt gac att tcc atg gtc ggg aga aat gcc cag               590
Leu Val Glu Ala Lys Arg Asp Ile Ser Met Val Gly Arg Asn Ala Gln
160                 165                 170                 175 ctt gcg agt gag aag gtg aag acg ctg aca gca gac ata agc cat atc               638
Leu Ala Ser Glu Lys Val Lys Thr Leu Thr Ala Asp Ile Ser His Ile
                180                 185                 190 aag agt aag tta cag gaa atc tcc aag atg ctg gag aag cca aag cca               686
Lys Ser Lys Leu Gln Glu Ile Ser Lys Met Leu Glu Lys Pro Lys Pro
            195                 200                 205 tag acctcaacat acgcgaggac atcgaagccc tggctgcagc ttggcggacg                    739
gggctgcgcc tcccagtgaa gatggccacg tgtgtgcacc acgtgtgttg tgagcctaag            799
gcgtgacaca gtgggtggct gtgtcagcag ggaccacgaa agtgtgtcag cgtgttgttg            859
gcagcatgtg tagcaccgtg aacgcgtgtg actgtcctgt ggtatgttgt gtgtaaatgt            919
gtcacggcag agccgtggcg ggggcacccc acgtgtcact gtaattgtgg gtgccctgtc            979
actacctgtg ttggtgtgaa caggtgtctg ccaacgagcg actgaggatg tcacggaggg           1039
ggttcggagc atgtacacat gtatgtccat tgttcccgc gctcacgttg tgtgatttgt            1099
gaagataaag gccgatggaa aagaa                                                 1124

<210> SEQ ID NO 4
<211> LENGTH: 207
<212> TYPE: PRT
<213> ORGANISM: Canis familiaris

<400> SEQUENCE: 4

Met Glu Ser Glu Glu Ile Tyr Thr Asn Gln Lys Val Glu Met Gln Ala
1               5                   10                  15

Ala Phe Lys Asp Lys Lys Gln Arg Val Pro Ala Asp Lys Glu Gly Ala
            20                  25                  30

Asp Asn Pro Asp Tyr Glu Asn Ile Thr Leu Ala Phe Arg Asn Gln Asp
        35                  40                  45

Gln Pro Lys Gly Ser His Leu Pro Lys Asn Gln Ser Lys Gln Pro
    50                  55                  60

Pro Ala Arg Thr His His Thr Ala Leu Gly Gly Ala His Val Pro Thr
65                  70                  75                  80

Leu Ser Arg Leu Pro Ser Asp Ser Gly Gln Leu Pro Arg Cys Leu His
                85                  90                  95

Arg Val Ile Met Ser Leu Tyr Met Leu Leu Ala Leu Ser Cys Ile Ile
            100                 105                 110

Leu Leu Val Leu Val Leu Met Lys Asn Leu Glu Met Ser Gln Glu Leu
        115                 120                 125

Leu Ala Leu Lys Arg Glu Leu Trp Asn Val Ser Val Ser Val Gln Glu
```

```
                130             135             140
Cys Gln Glu Gln Gln Asn Gln Gly Trp Ser Thr Val Arg Gln Leu Leu
145                 150                 155                 160

Val Glu Ala Lys Arg Asp Ile Ser Met Val Gly Arg Asn Ala Gln Leu
                165                 170                 175

Ala Ser Glu Lys Val Lys Thr Leu Thr Ala Asp Ile Ser His Ile Lys
            180                 185                 190

Ser Lys Leu Gln Glu Ile Ser Lys Met Leu Glu Lys Pro Lys Pro
            195                 200                 205

<210> SEQ ID NO 5
<211> LENGTH: 1416
<212> TYPE: DNA
<213> ORGANISM: Felis catus
<220> FEATURE:
<221> NAME/KEY: CDS
<222> LOCATION: (24)..(641)

<400> SEQUENCE: 5
tctgcttgaa tcaggaggtc agg atg caa gca gca gac ttc aaa ggc aag aaa    53
                         Met Gln Ala Ala Asp Phe Lys Gly Lys Lys
                          1               5                  10 cag agg gcc cca gac cat aag gaa ggt tcg gta cct caa ggt gca gac    101
Gln Arg Ala Pro Asp His Lys Glu Gly Ser Val Pro Gln Gly Ala Asp
             15                  20                  25 cct gac tat gag aat atc acc ttg acc ttc aga aac cag gag caa cca    149
Pro Asp Tyr Glu Asn Ile Thr Leu Thr Phe Arg Asn Gln Glu Gln Pro
         30                  35                  40 agg ggc agc cat tca cca ccc aag aat cga ggc aag cag cca cct gcc    197
Arg Gly Ser His Ser Pro Pro Lys Asn Arg Gly Lys Gln Pro Pro Ala
     45                  50                  55 agc ccg cac ctc aca gcc tcg gga ggg gcc cct gtc cca gcc tgg tcg    245
Ser Pro His Leu Thr Ala Ser Gly Gly Ala Pro Val Pro Ala Trp Ser
 60                  65                  70 aag cag gcc cca gac tct gcc cag gtc cct cgt tgg ctg cac aga gtc    293
Lys Gln Ala Pro Asp Ser Ala Gln Val Pro Arg Trp Leu His Arg Val
75                  80                  85                  90 acc ctg agc ctg tac atc ctc ctt gcc ctg ttc tgc atc gtt ctc ttg    341
Thr Leu Ser Leu Tyr Ile Leu Leu Ala Leu Phe Cys Ile Val Leu Leu
                 95                 100                 105 gcc ttg gtc ctg gtg aag aat tct gag gtg tcc cag gag ctg ctg gtc    389
Ala Leu Val Leu Val Lys Asn Ser Glu Val Ser Gln Glu Leu Leu Val
            110                 115                 120 gtg aaa agg gag ctc cag aat gtc tcc atc tcg gga caa cag tgt cag    437
Val Lys Arg Glu Leu Gln Asn Val Ser Ile Ser Gly Gln Gln Cys Gln
        125                 130                 135 gag gag cag aaa cag ggc tgg agc agc gtc cag cag ctc atc acg gag    485
Glu Glu Gln Lys Gln Gly Trp Ser Ser Val Gln Gln Leu Ile Thr Glu
        140                 145                 150 gcc agg cag gac att gac atg atc aag aga aat gtc cac atc ggg aac    533
Ala Arg Gln Asp Ile Asp Met Ile Lys Arg Asn Val His Ile Gly Asn
155                 160                 165                 170 gag aaa gtg aag acg ctg tca aca gac tta agc caa atc aag act aaa    581
Glu Lys Val Lys Thr Leu Ser Thr Asp Leu Ser Gln Ile Lys Thr Lys
                175                 180                 185 tta cat gaa atc tcc aag ata cta gag aag aag ccg cag cca cag ccc    629
Leu His Glu Ile Ser Lys Ile Leu Glu Lys Lys Pro Gln Pro Gln Pro
            190                 195                 200 aca gct caa taa atgagaagac attgacaccc aggctgcagc ttggaggacg        681
Thr Ala Gln
```

```
                                  205 gggctgcact tccccgtgaa gacggccgca tgtgtgcctc atggtgtcac gggagcgata      741 acacatgata cagtgggcgg ctgtgtcagc aaggaccgca gaagtgtgtc agcctgggcg      801 cgggtgttgg taacacgtgt tgcactgtga acacgtgtga atgtcctgtg gtatgttgtg      861 tgtgaatgtc atggagctgt gtgtgtgtgt gcgcgtgcgt gtgtgtgtgt ggagcacccc      921 ctacatcact gtaactgcgg gtgttgaggg tgtaccccgt cactcccgtg gttgtgtgaa      981 caggtgggtg tcagtgtgtg actgattatg tcaccgaggg tgtgcagagc gggtacattt     1041 gtgcgttccc ttgtttctgc actcacgttt tgtgatttgt gacgataaag gccaatggga     1101 aagaatgtgg ctttcagatc tgttcctggg agcatctggg ggtgggggtg gggacccggt     1161 ggcggagggt ctgcaagtat taagggatga ggaaagtcac acagcaagca cgcggacgtg     1221 ataaccagga gccctggggg cacgagtgtg tgtgagcatg aatgccctga atgggtcctt     1281 ttgtgcccat gaacttgtac ccagcaagga acagtctccg tgtctgagac tgtgtgccca     1341 gcagggtttg tggcccgaga tatacactgt ttccctaagt ggggctcctg ggtggctcag     1401 tcggttaagc gtccg                                                      1416

<210> SEQ ID NO 6
<211> LENGTH: 205
<212> TYPE: PRT
<213> ORGANISM: Felis catus

<400> SEQUENCE: 6

Met Gln Ala Ala Asp Phe Lys Gly Lys Lys Gln Arg Ala Pro Asp His
1               5                  10                  15

Lys Glu Gly Ser Val Pro Gln Gly Ala Asp Pro Asp Tyr Glu Asn Ile
            20                  25                  30

Thr Leu Thr Phe Arg Asn Gln Glu Gln Pro Arg Gly Ser His Ser Pro
        35                  40                  45

Pro Lys Asn Arg Gly Lys Gln Pro Pro Ala Ser Pro His Leu Thr Ala
    50                  55                  60

Ser Gly Gly Ala Pro Val Pro Ala Trp Ser Lys Gln Ala Pro Asp Ser
65                  70                  75                  80

Ala Gln Val Pro Arg Trp Leu His Arg Val Thr Leu Ser Leu Tyr Ile
                85                  90                  95

Leu Leu Ala Leu Phe Cys Ile Val Leu Ala Leu Val Leu Val Lys
            100                 105                 110

Asn Ser Glu Val Ser Gln Glu Leu Leu Val Val Lys Arg Glu Leu Gln
        115                 120                 125

Asn Val Ser Ile Ser Gly Gln Gln Cys Gln Glu Glu Gln Lys Gln Gly
    130                 135                 140

Trp Ser Ser Val Gln Gln Leu Ile Thr Glu Ala Arg Gln Asp Ile Asp
145                 150                 155                 160

Met Ile Lys Arg Asn Val His Ile Gly Asn Glu Lys Val Lys Thr Leu
                165                 170                 175

Ser Thr Asp Leu Ser Gln Ile Lys Thr Lys Leu His Glu Ile Ser Lys
            180                 185                 190

Ile Leu Glu Lys Lys Pro Gln Pro Gln Pro Thr Ala Gln
        195                 200                 205

<210> SEQ ID NO 7
<211> LENGTH: 1132
<212> TYPE: DNA
```

<213> ORGANISM: Mus musculus
<220> FEATURE:
<221> NAME/KEY: CDS
<222> LOCATION: (21)..(572)

<400> SEQUENCE: 7

```
acgtgaatca accaagcaga atg cat gca tca gcc tcc cag gat aag aac cgg        53
                      Met His Ala Ser Ala Ser Gln Asp Lys Asn Arg
                       1               5                  10 agg aag cca ggt cat gat gaa ggt gct cac aat cct gac tac gag aat         101
Arg Lys Pro Gly His Asp Glu Gly Ala His Asn Pro Asp Tyr Glu Asn
         15                  20                  25 ata acc ttg gcc ttc aga aac aag gac caa ctc aaa ctc agc caa tca         149
Ile Thr Leu Ala Phe Arg Asn Lys Asp Gln Leu Lys Leu Ser Gln Ser
     30                  35                  40 aca ccc aca aaa caa gcc aag ttc aag aca tcc ctg gac cca gct gag         197
Thr Pro Thr Lys Gln Ala Lys Phe Lys Thr Ser Leu Asp Pro Ala Glu
 45                  50                  55 tcc ccg cct tgg ttg tac aga acc att atg atg ttg tat gtt ctc ctt         245
Ser Pro Pro Trp Leu Tyr Arg Thr Ile Met Met Leu Tyr Val Leu Leu
 60                  65                  70                  75 gct ctc gtc ttt tta tcc tgc atc gtc ctc tct gct ttg gtc ttg gtg         293
Ala Leu Val Phe Leu Ser Cys Ile Val Leu Ser Ala Leu Val Leu Val
                 80                  85                  90 aaa aat tct gag atg tcc aag gag ctg tgg acc ttg aaa gca gag ctt         341
Lys Asn Ser Glu Met Ser Lys Glu Leu Trp Thr Leu Lys Ala Glu Leu
             95                 100                 105 tcg aat gtt tca gac acg gtg tgg aat atc cgg gag ctc cag aat cag         389
Ser Asn Val Ser Asp Thr Val Trp Asn Ile Arg Glu Leu Gln Asn Gln
         110                 115                 120 caa acg agg att tgg gaa gct gcc cag ggg gac atc aag gag gtc aag         437
Gln Thr Arg Ile Trp Glu Ala Ala Gln Gly Asp Ile Lys Glu Val Lys
     125                 130                 135 aag acc ctt ggc aca gtc atg agt agc atc cag act gga aac gac cgg         485
Lys Thr Leu Gly Thr Val Met Ser Ser Ile Gln Thr Gly Asn Asp Arg
140                 145                 150                 155 ctg aag act gtg ccg gca gat ata acc caa atc aag aaa act ctt gag         533
Leu Lys Thr Val Pro Ala Asp Ile Thr Gln Ile Lys Lys Thr Leu Glu
                 160                 165                 170 gcg cta gaa aag aag gca cag cct cag ccc agt aca taa gaggacacca         582
Ala Leu Glu Lys Lys Ala Gln Pro Gln Pro Ser Thr
             175                 180 cagcagtacc tgtgaagact ccgaattgca cctgctagtg aagatggcag atgggggtgg       642
gtactgagct tgagtgtgaa cctgccgtgc atcctcatat aaaaaagatt ctccaccagg       702
gggaatgagt gttgaagagg tgtgtatgca aatgagcatt tggggtttcc atgtattcca       762
ggagaagggt ttatggtgga aagagaacat ggcagtcaca gcaggtgtta ctctttatgg       822
gccacatagg tgtatgccct ggcttatgtg agtataggca tgtcctggtt ggcagctatt       882
cccgagaagt ccccaaagtg taagtgacat gtaggacatg cctccccatt ctcttgctca       942
tgtatgtgca tctggctgtt ctgtatgtgt gtcactgaag tggtgggtga tagacatcac      1002
cctggagatg tgtcatggca tgggtcattc ctagtgtttt tggtcatgtc agcttgtgtg      1062
ttcagggcat gcacacaaat gtagccatcg atttctgcac ttgtatttat gattcaagaa      1122
gataaatgcc                                                             1132
```

<210> SEQ ID NO 8
<211> LENGTH: 183
<212> TYPE: PRT

<213> ORGANISM: Mus musculus

<400> SEQUENCE: 8

```
Met His Ala Ser Ala Ser Gln Asp Lys Asn Arg Arg Lys Pro Gly His
1               5                   10                  15

Asp Glu Gly Ala His Asn Pro Asp Tyr Glu Asn Ile Thr Leu Ala Phe
            20                  25                  30

Arg Asn Lys Asp Gln Leu Lys Leu Ser Gln Ser Thr Pro Thr Lys Gln
        35                  40                  45

Ala Lys Phe Lys Thr Ser Leu Asp Pro Ala Glu Ser Pro Pro Trp Leu
    50                  55                  60

Tyr Arg Thr Ile Met Met Leu Tyr Val Leu Leu Ala Leu Val Phe Leu
65                  70                  75                  80

Ser Cys Ile Val Leu Ser Ala Leu Val Leu Val Lys Asn Ser Glu Met
                85                  90                  95

Ser Lys Glu Leu Trp Thr Leu Lys Ala Glu Leu Ser Asn Val Ser Asp
            100                 105                 110

Thr Val Trp Asn Ile Arg Glu Leu Gln Asn Gln Gln Thr Arg Ile Trp
        115                 120                 125

Glu Ala Ala Gln Gly Asp Ile Lys Glu Val Lys Lys Thr Leu Gly Thr
    130                 135                 140

Val Met Ser Ser Ile Gln Thr Gly Asn Asp Arg Leu Lys Thr Val Pro
145                 150                 155                 160

Ala Asp Ile Thr Gln Ile Lys Lys Thr Leu Glu Ala Leu Glu Lys Lys
                165                 170                 175

Ala Gln Pro Gln Pro Ser Thr
            180
```

<210> SEQ ID NO 9
<211> LENGTH: 249
<212> TYPE: DNA
<213> ORGANISM: Homo sapiens
<220> FEATURE:
<221> NAME/KEY: CDS
<222> LOCATION: (1)..(249)

<400> SEQUENCE: 9

```
gtg aag aat gct gag atg tcc aag gag ctg ctg ggc ttt aaa agg gag      48
Val Lys Asn Ala Glu Met Ser Lys Glu Leu Leu Gly Phe Lys Arg Glu
1               5                   10                  15 ctt tgg aat gtc tca aac tcc gta caa gca tgc gaa gag aga cag aag      96
Leu Trp Asn Val Ser Asn Ser Val Gln Ala Cys Glu Glu Arg Gln Lys
            20                  25                  30 aga ggc tgg gat tcc gtt cag cag agc atc acc atg gtc agg agc aag     144
Arg Gly Trp Asp Ser Val Gln Gln Ser Ile Thr Met Val Arg Ser Lys
        35                  40                  45 att gat aga tta gag acg aca tta gca ggc ata aaa aac att gac aca     192
Ile Asp Arg Leu Glu Thr Thr Leu Ala Gly Ile Lys Asn Ile Asp Thr
    50                  55                  60 aag gta cag aaa atc ttg gag gtg ctg cag aaa atg cca cag tcc tca     240
Lys Val Gln Lys Ile Leu Glu Val Leu Gln Lys Met Pro Gln Ser Ser
65                  70                  75                  80 cct caa taa                                                         249
Pro Gln
```

<210> SEQ ID NO 10
<211> LENGTH: 82
<212> TYPE: PRT
<213> ORGANISM: Homo sapiens -continued

```
<400> SEQUENCE: 10

Val Lys Asn Ala Glu Met Ser Lys Glu Leu Leu Gly Phe Lys Arg Glu
1               5                   10                  15

Leu Trp Asn Val Ser Asn Ser Val Gln Ala Cys Glu Glu Arg Gln Lys
            20                  25                  30

Arg Gly Trp Asp Ser Val Gln Gln Ser Ile Thr Met Val Arg Ser Lys
        35                  40                  45

Ile Asp Arg Leu Glu Thr Thr Leu Ala Gly Ile Lys Asn Ile Asp Thr
    50                  55                  60

Lys Val Gln Lys Ile Leu Glu Val Leu Gln Lys Met Pro Gln Ser Ser
65                  70                  75                  80

Pro Gln

<210> SEQ ID NO 11
<211> LENGTH: 267
<212> TYPE: DNA
<213> ORGANISM: Canis familiaris
<220> FEATURE:
<221> NAME/KEY: CDS
<222> LOCATION: (1)..(267)

<400> SEQUENCE: 11 aag aat ctg gag atg tcc cag gag ttg ctg gcc ctg aaa agg gag ctc      48
Lys Asn Leu Glu Met Ser Gln Glu Leu Leu Ala Leu Lys Arg Glu Leu
1               5                   10                  15 tgg aat gtg tcc gtc tcg gtg caa gag tgc cag gag cag cag aat cag      96
Trp Asn Val Ser Val Ser Val Gln Glu Cys Gln Glu Gln Gln Asn Gln
            20                  25                  30 ggc tgg agc acc gtc cgg cag ctc ctg gtg gag gcc aag cgt gac att     144
Gly Trp Ser Thr Val Arg Gln Leu Leu Val Glu Ala Lys Arg Asp Ile
        35                  40                  45 tcc atg gtc ggg aga aat gcc cag ctt gcg agt gag aag gtg aag acg     192
Ser Met Val Gly Arg Asn Ala Gln Leu Ala Ser Glu Lys Val Lys Thr
    50                  55                  60 ctg aca gca gac ata agc cat atc aag agt aag tta cag gaa atc tcc     240
Leu Thr Ala Asp Ile Ser His Ile Lys Ser Lys Leu Gln Glu Ile Ser
65                  70                  75                  80 aag atg ctg gag aag cca aag cca tag                                 267
Lys Met Leu Glu Lys Pro Lys Pro
                85

<210> SEQ ID NO 12
<211> LENGTH: 88
<212> TYPE: PRT
<213> ORGANISM: Canis familiaris

<400> SEQUENCE: 12

Lys Asn Leu Glu Met Ser Gln Glu Leu Leu Ala Leu Lys Arg Glu Leu
1               5                   10                  15

Trp Asn Val Ser Val Ser Val Gln Glu Cys Gln Glu Gln Gln Asn Gln
            20                  25                  30

Gly Trp Ser Thr Val Arg Gln Leu Leu Val Glu Ala Lys Arg Asp Ile
        35                  40                  45

Ser Met Val Gly Arg Asn Ala Gln Leu Ala Ser Glu Lys Val Lys Thr
    50                  55                  60

Leu Thr Ala Asp Ile Ser His Ile Lys Ser Lys Leu Gln Glu Ile Ser
65                  70                  75                  80

Lys Met Leu Glu Lys Pro Lys Pro
```

<210> SEQ ID NO 13
<211> LENGTH: 285
<212> TYPE: DNA
<213> ORGANISM: Felis catus
<220> FEATURE:
<221> NAME/KEY: CDS
<222> LOCATION: (1)..(285)

<400> SEQUENCE: 13

| | | | | | | | | | | | | | | | | |
|---|---|---|---|---|---|---|---|---|---|---|---|---|---|---|---|---|
| aag | aat | tct | gag | gtg | tcc | cag | gag | ctg | ctg | gtc | gtg | aaa | agg | gag | ctc | 48 |
| Lys | Asn | Ser | Glu | Val | Ser | Gln | Glu | Leu | Leu | Val | Val | Lys | Arg | Glu | Leu | |
| 1 | | | | 5 | | | | | 10 | | | | | 15 | | |
| cag | aat | gtc | tcc | atc | tcg | gga | caa | cag | tgt | cag | gag | gag | cag | aaa | cag | 96 |
| Gln | Asn | Val | Ser | Ile | Ser | Gly | Gln | Gln | Cys | Gln | Glu | Glu | Gln | Lys | Gln | |
| | | | 20 | | | | | 25 | | | | | 30 | | | |
| ggc | tgg | agc | agc | gtc | cag | cag | ctc | atc | acg | gag | gcc | agg | cag | gac | att | 144 |
| Gly | Trp | Ser | Ser | Val | Gln | Gln | Leu | Ile | Thr | Glu | Ala | Arg | Gln | Asp | Ile | |
| | | 35 | | | | | 40 | | | | | 45 | | | | |
| gac | atg | atc | aag | aga | aat | gtc | cac | atc | ggg | aac | gag | aaa | gtg | aag | acg | 192 |
| Asp | Met | Ile | Lys | Arg | Asn | Val | His | Ile | Gly | Asn | Glu | Lys | Val | Lys | Thr | |
| | 50 | | | | | 55 | | | | | 60 | | | | | |
| ctg | tca | aca | gac | tta | agc | caa | atc | aag | act | aaa | tta | cat | gaa | atc | tcc | 240 |
| Leu | Ser | Thr | Asp | Leu | Ser | Gln | Ile | Lys | Thr | Lys | Leu | His | Glu | Ile | Ser | |
| 65 | | | | | 70 | | | | | 75 | | | | | 80 | |
| aag | ata | cta | gag | aag | aag | ccg | cag | cca | cag | ccc | aca | gct | caa | taa | | 285 |
| Lys | Ile | Leu | Glu | Lys | Lys | Pro | Gln | Pro | Gln | Pro | Thr | Ala | Gln | | | |
| | | | | 85 | | | | | 90 | | | | | | | |

<210> SEQ ID NO 14
<211> LENGTH: 94
<212> TYPE: PRT
<213> ORGANISM: Felis catus

<400> SEQUENCE: 14

Lys Asn Ser Glu Val Ser Gln Glu Leu Leu Val Val Lys Arg Glu Leu
1               5                   10                  15

Gln Asn Val Ser Ile Ser Gly Gln Gln Cys Gln Glu Glu Gln Lys Gln
            20                  25                  30

Gly Trp Ser Ser Val Gln Gln Leu Ile Thr Glu Ala Arg Gln Asp Ile
        35                  40                  45

Asp Met Ile Lys Arg Asn Val His Ile Gly Asn Glu Lys Val Lys Thr
    50                  55                  60

Leu Ser Thr Asp Leu Ser Gln Ile Lys Thr Lys Leu His Glu Ile Ser
65                  70                  75                  80

Lys Ile Leu Glu Lys Lys Pro Gln Pro Gln Pro Thr Ala Gln
                85                  90

<210> SEQ ID NO 15
<211> LENGTH: 279
<212> TYPE: DNA
<213> ORGANISM: Mus musculus
<220> FEATURE:
<221> NAME/KEY: CDS
<222> LOCATION: (1)..(279)

<400> SEQUENCE: 15

| | | | | | | | | | | | | | | | | |
|---|---|---|---|---|---|---|---|---|---|---|---|---|---|---|---|---|
| aaa | aat | tct | gag | atg | tcc | aag | gag | ctg | tgg | acc | ttg | aaa | gca | gag | ctt | 48 |
| Lys | Asn | Ser | Glu | Met | Ser | Lys | Glu | Leu | Trp | Thr | Leu | Lys | Ala | Glu | Leu | |
| 1 | | | | 5 | | | | | 10 | | | | | 15 | | |
| tcg | aat | gtt | tca | gac | acg | gtg | tgg | aat | atc | cgg | gag | ctc | cag | aat | cag | 96 |

```
Ser Asn Val Ser Asp Thr Val Trp Asn Ile Arg Glu Leu Gln Asn Gln
             20                  25                  30 caa acg agg att tgg gaa gct gcc cag ggg gac atc aag gag gtc aag     144
Gln Thr Arg Ile Trp Glu Ala Ala Gln Gly Asp Ile Lys Glu Val Lys
         35                  40                  45 aag acc ctt ggc aca gtc atg agt agc atc cag act gga aac gac cgg     192
Lys Thr Leu Gly Thr Val Met Ser Ser Ile Gln Thr Gly Asn Asp Arg
 50                  55                  60 ctg aag act gtg ccg gca gat ata acc caa atc aag aaa act ctt gag     240
Leu Lys Thr Val Pro Ala Asp Ile Thr Gln Ile Lys Lys Thr Leu Glu
 65                  70                  75                  80 gcg cta gaa aag aag gca cag cct cag ccc agt aca taa                 279
Ala Leu Glu Lys Lys Ala Gln Pro Gln Pro Ser Thr
                 85                  90

<210> SEQ ID NO 16
<211> LENGTH: 92
<212> TYPE: PRT
<213> ORGANISM: Mus musculus

<400> SEQUENCE: 16

Lys Asn Ser Glu Met Ser Lys Glu Leu Trp Thr Leu Lys Ala Glu Leu
  1               5                  10                  15

Ser Asn Val Ser Asp Thr Val Trp Asn Ile Arg Glu Leu Gln Asn Gln
             20                  25                  30

Gln Thr Arg Ile Trp Glu Ala Ala Gln Gly Asp Ile Lys Glu Val Lys
         35                  40                  45

Lys Thr Leu Gly Thr Val Met Ser Ser Ile Gln Thr Gly Asn Asp Arg
 50                  55                  60

Leu Lys Thr Val Pro Ala Asp Ile Thr Gln Ile Lys Lys Thr Leu Glu
 65                  70                  75                  80

Ala Leu Glu Lys Lys Ala Gln Pro Gln Pro Ser Thr
                 85                  90

<210> SEQ ID NO 17
<211> LENGTH: 20
<212> TYPE: DNA
<213> ORGANISM: Artificial
<220> FEATURE:
<223> OTHER INFORMATION: T3 primer

<400> SEQUENCE: 17
aattaaccct cactaaaggg                                                20

<210> SEQ ID NO 18
<211> LENGTH: 19
<212> TYPE: DNA
<213> ORGANISM: Artificial
<220> FEATURE:
<223> OTHER INFORMATION: T7 primer

<400> SEQUENCE: 18
taatacgact cactatagg                                                 19

<210> SEQ ID NO 19
<211> LENGTH: 20
<212> TYPE: DNA
<213> ORGANISM: Artificial
<220> FEATURE:
<223> OTHER INFORMATION: canis RT primer sense

<400> SEQUENCE: 19
```
ccacgtccca accctgtcta                                               20

<210> SEQ ID NO 20
<211> LENGTH: 20
<212> TYPE: DNA
<213> ORGANISM: Artificial
<220> FEATURE:
<223> OTHER INFORMATION: canis RT primer antisense

<400> SEQUENCE: 20
gtgctccagc cctgattctg                                               20

<210> SEQ ID NO 21
<211> LENGTH: 20
<212> TYPE: DNA
<213> ORGANISM: Artificial
<220> FEATURE:
<223> OTHER INFORMATION: human RT primer sense

<400> SEQUENCE: 21
tggccttcaa aaatcaggac                                               20

<210> SEQ ID NO 22
<211> LENGTH: 21
<212> TYPE: DNA
<213> ORGANISM: Artificial
<220> FEATURE:
<223> OTHER INFORMATION: human RT primer antisense

<400> SEQUENCE: 22
aggctcagga tggctctgta c                                             21

<210> SEQ ID NO 23
<211> LENGTH: 20
<212> TYPE: DNA
<213> ORGANISM: Artificial
<220> FEATURE:
<223> OTHER INFORMATION: mouse RT primer sense

<400> SEQUENCE: 23
tccaaggagc tgtggacctt                                               20

<210> SEQ ID NO 24
<211> LENGTH: 20
<212> TYPE: DNA
<213> ORGANISM: Artificial
<220> FEATURE:
<223> OTHER INFORMATION: mouse  RT primer antisense

<400> SEQUENCE: 24
agtcttcagc cggtcgtttc                                               20

<210> SEQ ID NO 25
<211> LENGTH: 39
<212> TYPE: DNA
<213> ORGANISM: Artificial
<220> FEATURE:
<223> OTHER INFORMATION: human MCEMP1 EcoRI primer sense

<400> SEQUENCE: 25
gaattcgccg ccaccatgga agtggaggaa atctacaag                          39

<210> SEQ ID NO 26
<211> LENGTH: 29
<212> TYPE: DNA
<213> ORGANISM: Artificial

```
<220> FEATURE:
<223> OTHER INFORMATION: human MCEMP1 NotI primer antisense

<400> SEQUENCE: 26
gcggccgctt attgaggtga ggactgtgg                                        29

<210> SEQ ID NO 27
<211> LENGTH: 28
<212> TYPE: DNA
<213> ORGANISM: Artificial
<220> FEATURE:
<223> OTHER INFORMATION: human MCEMP1ECD KpnI primer sense

<400> SEQUENCE: 27
ggtaccaaga atgctgagat gtccaagg                                         28

<210> SEQ ID NO 28
<211> LENGTH: 27
<212> TYPE: DNA
<213> ORGANISM: Artificial
<220> FEATURE:
<223> OTHER INFORMATION: human MCEMP1ECD EcoRI primer antisense

<400> SEQUENCE: 28
gaattcggtt gaggtgagga ctgtggc                                          27

<210> SEQ ID NO 29
<211> LENGTH: 960
<212> TYPE: DNA
<213> ORGANISM: Artificial
<220> FEATURE:
<223> OTHER INFORMATION: Fc fusion protein
<220> FEATURE:
<221> NAME/KEY: CDS
<222> LOCATION: (1)..(960)

<400> SEQUENCE: 29 aag aat gct gag atg tcc aag gag ctg ctg ggc ttt aaa agg gag ctt        48
Lys Asn Ala Glu Met Ser Lys Glu Leu Leu Gly Phe Lys Arg Glu Leu
1               5                   10                  15 tgg aat gtc tca aac tcc gta caa gca tgc gaa gag aga cag aag aga        96
Trp Asn Val Ser Asn Ser Val Gln Ala Cys Glu Glu Arg Gln Lys Arg
            20                  25                  30 ggc tgg gat tcc gtt cag cag agc atc acc atg gtc agg agc aag att       144
Gly Trp Asp Ser Val Gln Gln Ser Ile Thr Met Val Arg Ser Lys Ile
        35                  40                  45 gat aga tta gag acg aca tta gca ggc ata aaa aac att gac aca aag       192
Asp Arg Leu Glu Thr Thr Leu Ala Gly Ile Lys Asn Ile Asp Thr Lys
    50                  55                  60 gta cag aaa atc ttg gag gtg ctg cag aaa atg cca cag tcc tca cct       240
Val Gln Lys Ile Leu Glu Val Leu Gln Lys Met Pro Gln Ser Ser Pro
65                  70                  75                  80 caa ccg aat tct gca gat atc ccc aga ggg ccc aca atc aag ccc tgt       288
Gln Pro Asn Ser Ala Asp Ile Pro Arg Gly Pro Thr Ile Lys Pro Cys
                85                  90                  95 cct cca tgc aaa tgc cca gca cct aac ctc ttg ggt gga cca tcc gtc       336
Pro Pro Cys Lys Cys Pro Ala Pro Asn Leu Leu Gly Gly Pro Ser Val
            100                 105                 110 ttc atc ttc cct cca aag atc aag gat gta ctc atg atc tcc ctg agc       384
Phe Ile Phe Pro Pro Lys Ile Lys Asp Val Leu Met Ile Ser Leu Ser
        115                 120                 125 ccc ata gtc aca tgt gtg gtg gtg gat gtg agc gag gat gac cca gat       432
Pro Ile Val Thr Cys Val Val Val Asp Val Ser Glu Asp Asp Pro Asp
    130                 135                 140
```

```
gtc cag atc agc tgg ttt gtg aac aac gtg gaa gta cac aca gct cag        480
Val Gln Ile Ser Trp Phe Val Asn Asn Val Glu Val His Thr Ala Gln
145                 150                 155                 160 aca caa acc cat aga gag gat tac aac agt act ctc cgg gtg gtc agt        528
Thr Gln Thr His Arg Glu Asp Tyr Asn Ser Thr Leu Arg Val Val Ser
                165                 170                 175 gcc ctc ccc atc cag cac cag gac tgg atg agt ggc aag gag ttc aaa        576
Ala Leu Pro Ile Gln His Gln Asp Trp Met Ser Gly Lys Glu Phe Lys
            180                 185                 190 tgc aag gtc aac aac aaa gac ctc cca gcg ccc atc gag aga acc atc        624
Cys Lys Val Asn Asn Lys Asp Leu Pro Ala Pro Ile Glu Arg Thr Ile
        195                 200                 205 tca aaa ccc aaa ggg tca gta aga gct cca cag gta tat gtc ttg cct        672
Ser Lys Pro Lys Gly Ser Val Arg Ala Pro Gln Val Tyr Val Leu Pro
    210                 215                 220 cca cca gaa gaa gag atg act aag aaa cag gtc act ctg acc tgc atg        720
Pro Pro Glu Glu Glu Met Thr Lys Lys Gln Val Thr Leu Thr Cys Met
225                 230                 235                 240 gtc aca gac ttc atg cct gaa gac att tac gtg gag tgg acc aac aac        768
Val Thr Asp Phe Met Pro Glu Asp Ile Tyr Val Glu Trp Thr Asn Asn
                245                 250                 255 ggg aaa aca gag cta aac tac aag aac act gaa cca gtc ctg gac tct        816
Gly Lys Thr Glu Leu Asn Tyr Lys Asn Thr Glu Pro Val Leu Asp Ser
            260                 265                 270 gat ggt tct tac ttc atg tac agc aag ctg aga gtg gaa aag aag aac        864
Asp Gly Ser Tyr Phe Met Tyr Ser Lys Leu Arg Val Glu Lys Lys Asn
        275                 280                 285 tgg gtg gaa aga aat agc tac tcc tgt tca gtg gtc cac gag ggt ctg        912
Trp Val Glu Arg Asn Ser Tyr Ser Cys Ser Val Val His Glu Gly Leu
    290                 295                 300 cac aat cac cac acg act aag agc ttc tcc cgg act ccg ggt aaa tga       960
His Asn His His Thr Thr Lys Ser Phe Ser Arg Thr Pro Gly Lys
305                 310                 315

<210> SEQ ID NO 30
<211> LENGTH: 319
<212> TYPE: PRT
<213> ORGANISM: Artificial
<220> FEATURE:
<223> OTHER INFORMATION: Fc fusion protein

<400> SEQUENCE: 30

Lys Asn Ala Glu Met Ser Lys Glu Leu Leu Gly Phe Lys Arg Glu Leu
1               5                   10                  15

Trp Asn Val Ser Asn Ser Val Gln Ala Cys Glu Glu Arg Gln Lys Arg
                20                  25                  30

Gly Trp Asp Ser Val Gln Gln Ser Ile Thr Met Val Arg Ser Lys Ile
            35                  40                  45

Asp Arg Leu Glu Thr Thr Leu Ala Gly Ile Lys Asn Ile Asp Thr Lys
        50                  55                  60

Val Gln Lys Ile Leu Glu Val Leu Gln Lys Met Pro Gln Ser Ser Pro
65                  70                  75                  80

Gln Pro Asn Ser Ala Asp Ile Pro Arg Gly Pro Thr Ile Lys Pro Cys
                85                  90                  95

Pro Pro Cys Lys Cys Pro Ala Pro Asn Leu Leu Gly Gly Pro Ser Val
            100                 105                 110

Phe Ile Phe Pro Pro Lys Ile Lys Asp Val Leu Met Ile Ser Leu Ser
        115                 120                 125
```

-continued

```
Pro Ile Val Thr Cys Val Val Val Asp Val Ser Glu Asp Asp Pro Asp
    130             135             140

Val Gln Ile Ser Trp Phe Val Asn Asn Val Glu Val His Thr Ala Gln
145             150              155                 160

Thr Gln Thr His Arg Glu Asp Tyr Asn Ser Thr Leu Arg Val Val Ser
            165             170             175

Ala Leu Pro Ile Gln His Gln Asp Trp Met Ser Gly Lys Glu Phe Lys
        180             185             190

Cys Lys Val Asn Asn Lys Asp Leu Pro Ala Pro Ile Glu Arg Thr Ile
    195             200             205

Ser Lys Pro Lys Gly Ser Val Arg Ala Pro Gln Val Tyr Val Leu Pro
    210             215             220

Pro Pro Glu Glu Glu Met Thr Lys Lys Gln Val Thr Leu Thr Cys Met
225             230             235             240

Val Thr Asp Phe Met Pro Glu Asp Ile Tyr Val Glu Trp Thr Asn Asn
            245             250             255

Gly Lys Thr Glu Leu Asn Tyr Lys Asn Thr Glu Pro Val Leu Asp Ser
            260             265             270

Asp Gly Ser Tyr Phe Met Tyr Ser Lys Leu Arg Val Glu Lys Lys Asn
        275             280             285

Trp Val Glu Arg Asn Ser Tyr Ser Cys Ser Val Val His Glu Gly Leu
    290             295             300

His Asn His His Thr Thr Lys Ser Phe Ser Arg Thr Pro Gly Lys
305             310             315
```

METHOD FOR TREATING CANCER BY ADMINISTRATION OF ANTIBODIES THAT BIND TO EXTRACELLULAR REGION PORTION OF MCEMP1 PROTEIN

TECHNICAL FIELD

The present invention relates to a novel medical use of antibodies to MCEMP1 or fragments thereof as, for example, therapeutic and/or preventive agents for cancer.

BACKGROUND ART

In recent years, a variety of antibody medicines for cancer treatment that target antigen proteins on cancer cells have come into existence. The antibody medicines used as cancer-specific therapeutic agents exhibit drug efficacy to a certain extent, and thus they have been gaining attention. However, many of target antigen proteins are also expressed on multiple normal cells. As a result of antibody administration, not only cancer cells, but also normal cells on which a target antigen has been expressed can be damaged, thereby causing a side effect, which becomes problematic. Hence, it is expected that, if it becomes possible to identify cancer antigens that are specifically expressed on the surface of a cancer cell and to use antibodies targeting such antigens as medicaments, then treatment with antibody medicines that cause fewer side effects could be realized.

It has been reported that Mast Cell-Expressed Membrane Protein 1 (MCEMP1), a type 2 transmembrane protein, is expressed on cell membranes in a manner specific for mast cells, suggesting the possibility that the protein participates in mast cell differentiation, immune response, and allergic response (Non Patent Literature 1). However, none of the previous reports show that the MCEMP1 protein has immunity inducing activity against cancer cells and is thereby useful for treatment or prevention of cancers.

PRIOR ART LITERATURE

Non Patent Literature

Non Patent Literature 1: Kang Li. et al. Genomics, 86:68-75 (2005)

SUMMARY OF INVENTION

Technical Problem

An object of the present invention is to identify cancer antigen proteins specifically expressed on the surface of cancer cells and to provide a use of antibodies targeting such proteins as therapeutic and/or preventive agents for cancer.

Solution to Problem

As a result of intensive studies, the present inventors have now obtained cDNA encoding a protein that binds to an antibody present in the serum from a tumor-bearing organism by the SEREX method using canine testis tissue-derived cDNA libraries and sera from dogs with leukemia. With the use of the obtained canine genes and genes homologs from human, feline, and mouse, MCEMP1 proteins having amino acid sequences shown in SEQ ID NO: 2, 4, 6 or 8 and antibodies against the MCEMP1 proteins have now been prepared. In addition, the present inventors have now found that MCEMP1 is specifically expressed in the cells of leukemia, myelodysplastic syndrome, osteosarcoma, thymoma, mastocytoma, or perianal adenocarcinoma, and that portions of the MCEMP1 proteins are specifically expressed on the surface of such cancer cells. Further, the present inventors have now found that antibodies against the MCEMP1 portions expressed on cancer cell surfaces can damage cancer cells expressing MCEMP1. These findings have led to the completion of the present invention.

Therefore, the present invention includes aspects below.

(1) A pharmaceutical composition for treatment and/or prevention of a cancer, which comprises, as an active ingredient, an antibody or fragment thereof having an immunological reactivity with an MCEMP1 protein having the amino acid sequence shown in SEQ ID NO: 2, 4, 6, or 8 or an amino acid sequence having 80% or more sequence identity with the amino acid sequence, or with a fragment of the MCEMP1 protein comprising 7 or more consecutive amino acids.

(2) The pharmaceutical composition according to (1), which comprises, as an active ingredient, an antibody or fragment thereof having an immunological reactivity with a polypeptide comprising an extracellular region portion of the MCEMP1 protein, the polypeptide being a polypeptide consisting of 7 or more consecutive amino acids of the amino acid sequence shown in SEQ ID NO: 10, 12, 14, or 16, or a polypeptide consisting of an amino acid sequence having 80% or more sequence identity with the amino acid sequence.

(3) The pharmaceutical composition according to (1) or (2), wherein the cancer is a cancer expressing MCEMP1 on a cell surface.

(4) The pharmaceutical composition according to any one of (1) to (3), wherein the cancer is selected from the group consisting of leukemia, myelodysplastic syndrome, osteosarcoma, thymoma, mastocytoma, and perianal adenocarcinoma.

(5) The pharmaceutical composition according to any one of (1) to (4), wherein the antibody is a monoclonal or polyclonal antibody.

(6) The pharmaceutical composition according to any one of (1) to (5), wherein the antibody is a human antibody, a humanized antibody, a chimeric antibody, a single chain antibody, or a multispecific antibody.

(7) An antibody or fragment thereof having an immunological reactivity with a polypeptide comprising an extracellular region portion of an MCEMP1 protein, the polypeptide being a polypeptide consisting of the amino acid sequence shown in SEQ ID NO: 10, 12, 14, or 16 or an amino acid sequence having 80% or more sequence identity with the amino acid sequence.

(8) The antibody or fragment thereof according to (7), wherein the antibody is a human antibody, a humanized antibody, a chimeric antibody, a single chain antibody, or a multispecific antibody.

(9) A pharmaceutical combination for treatment and/or prevention of a cancer, which comprises the pharmaceutical composition according to any one of (1) to (6) and a pharmaceutical composition comprising an antitumor agent.

(10) A method for treating and/or preventing a cancer, which comprises administering, to a subject, an antibody or fragment thereof having an immunological reactivity with an MCEMP1 protein having the amino acid sequence shown in SEQ ID NO: 2, 4, 6, or 8 or an amino acid sequence having 80% or more sequence identity with the amino acid sequence, or with a fragment of the MCEMP1 protein comprising 7 or more consecutive amino acids.

This description includes all or part of the contents disclosed in Japanese Patent Application No. 2016-064035, to which the present application claims the priority.

Advantageous Effects of Invention

Antibodies against MCEMP1 used in the present invention damage cancer cells. Therefore, such antibodies against MCEMP1 are useful for treatment or prevention of cancers.

BRIEF DESCRIPTION OF DRAWINGS

FIG. 2A shows the expression patterns of the human MCEMP1 gene in each of human tissues. FIG. 2B shows the expression patterns of the human MCEMP1 gene in each of human cancer cell lines.

DESCRIPTION OF EMBODIMENTS

Figure 1:
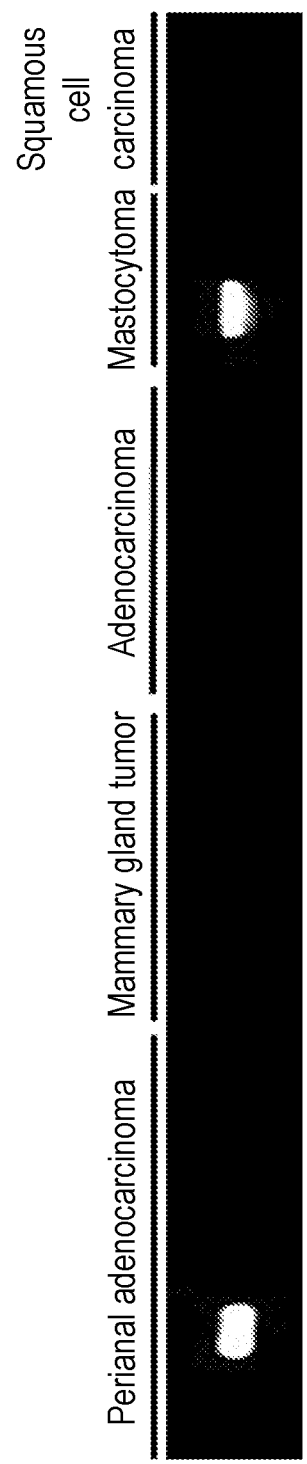
FIG. 1 shows expression patterns of the identified canine MCEMP1 gene in canine tumor tissues.

The present invention relates to a use of an antibody or fragment (preferably antigen binding fragment) thereof to an MCEMP1 protein or a fragment thereof for treatment and/or prevention of cancers.

The present invention relates to a pharmaceutical composition for treatment and/or prevention of a cancer, which comprises, as an active ingredient, an antibody or fragment thereof having an immunological reactivity with an MCEMP1 protein having an amino acid sequence shown in SEQ ID NO: 2, 4, 6, or 8 or an amino acid sequence having 80% or more (preferably 85% or more, more preferably 90% or more, further preferably 95% or more, and particularly preferably 99% or more, for example, 99.5% or more) sequence identity with the amino acid sequence, or with a fragment of the MCEMP1 protein comprising 7 or more (7 to each full-length sequence, preferably 7 to 150 and more preferably 7 to 50) consecutive amino acids.

The present invention also relates to the pharmaceutical composition for treatment and/or prevention of a cancer, which comprises, as an active ingredient, an antibody or fragment thereof having an immunological reactivity with a partial polypeptide of the MCEMP1 protein, the partial polypeptide being a polypeptide consisting of 7 or more (7 to each full-length sequence, preferably 7 to 40, more preferably 7 to 20, for example, 7 to 12 or 8 to 11) consecutive amino acids of an amino acid sequence shown in any one of the even numbered SEQ ID NOS: 10 to 24, or a polypeptide consisting of an amino acid sequence having 80% or more (preferably 85% or more, more preferably 90% or more, further preferably 95% or more, and particularly preferably 97% or more) sequence identity with the amino acid sequence.

The antitumor activity of the antibody or fragment thereof to the polypeptide consisting of an amino acid sequence shown in SEQ ID NO: 2, 4, 6, or 8 or to a fragment of the polypeptide used in the present invention can be evaluated by examining in vivo the inhibition of tumor growth in a tumor-bearing animal, or, as described below, by examining in vitro whether or not immunocyte- or complement-mediated cytotoxic activity against tumor cells expressing the polypeptide is exhibited.

Likewise, the antitumor activity of the antibody or fragment thereof against the polypeptide consisting of an amino acid sequence shown in any one of the even numbered SEQ ID NOS: 10 to 16 or a fragment of the polypeptide used in the present invention can be evaluated by examining in vivo the inhibition of tumor growth in a tumor-bearing animal, or, as described below, by examining in vitro whether or not immunocyte- or complement-mediated cytotoxic activity against tumor cells expressing the polypeptide is exhibited.

In addition, the nucleotide sequences of polynucleotides encoding the proteins consisting of the amino acid sequences shown in SEQ ID NOS: 2, 4, 6, 8, 10, 12, 14, and 16 are shown in SEQ ID NOS: 1, 3, 5, 7, 9, 11, 13, and 15 respectively.

The amino acid sequence shown in SEQ ID NO: 4 in the Sequence Listing disclosed according to the present invention is the amino acid sequence of the MCEMP1, which was isolated, by the SEREX method using canine testis tissue-derived cDNA libraries and sera from dogs with leukemia, as a polypeptide capable of binding to antibodies specifically existing in the sera from tumor-bearing dogs; the amino acid sequence shown in SEQ ID NO: 2 is the amino acid sequence of the MCEMP1 isolated as a human homolog of said dog polypeptide; the amino acid sequence shown in SEQ ID NO: 6 is the amino acid sequence of the MCEMP1 isolated as a feline homolog of said dog polypeptide; and the amino acid sequence shown in SEQ ID NO: 8 is the amino acid sequence of the MCEMP1 protein isolated as a mouse homolog of said dog polypeptide (see Example 1 described below).

According to the present invention, an antibody that binds to a portion expressed on cancer cell surfaces within MCEMP1 protein is preferably used. Specific examples thereof include an amino acid sequence shown in SEQ ID NO: 10 (human), 12 (canine), 14 (feline), or 16 (mouse), which is a polypeptide comprising an extracellular region portion of the MCEMP1 protein, or fragments thereof (preferably, the fragments each consisting of 7 or more consecutive amino acids of any one of the amino acid sequences), or an amino acid sequence having 80% or more, preferably 85% or more, more preferably 90% or more, further preferably 95% or more, and particularly preferably 99% or more sequence identity to any one of these polypeptides. Antibodies of the present invention include all antibodies capable of binding to the above polypeptides and having antitumor activity.

The antibodies to MCEMP1 usable in the present invention as described above may be any types thereof, as long as they can exhibit antitumor activity. Examples thereof can include monoclonal antibodies, polyclonal antibodies, synthetic antibodies, multispecific antibodies (e.g., bispecific antibodies), human antibodies, humanized antibodies, chimeric antibodies, and single-chain antibodies (scFV). The antibodies used in the present invention also include antibody fragments, for example, antigen binding fragments such as Fab and F(ab')$_2$. These antibodies and fragments thereof can be prepared by methods known to persons skilled in the art. In the present invention, antibodies or fragments thereof capable of specifically binding to an MCEMP1 protein are desirable. Such antibodies are preferably monoclonal antibodies; however, as long as homogenous antibodies can be stably produced, polyclonal antibodies may also be used. In addition, if the subject is a human, a human antibody or a humanized antibody is desirable in order to avoid or inhibit the immunorejection.

The word "specifically binding to an MCEMP1 protein or fragments thereof" as used herein means that an antibody of interest specifically binds to the MCEMP1 protein or fragments thereof and does not substantially bind to other proteins.

The antitumor activity of an antibody used in the present invention can be evaluated by examining in vivo the inhibition of tumor growth in a tumor-bearing animal, or, as described below, examining in vitro whether or not the immunocyte- or complement-mediated cytotoxic activity against tumor cells expressing the polypeptide is exhibited.

Moreover, the subjects in need of treatment and/or prevention of cancer according to the present invention are mammals such as human, pet animals, livestock animals, sport animals, or experimental animals. The preferred subject is a human.

Production of antigens, production of antibodies, and pharmaceutical compositions, related to the present invention, will be explained below.

<Production of Antigens Used for Antibody Production>

Proteins or fragments thereof used as sensitizing antigens for obtaining antibodies to MCEMP1 used in the present invention are not limited in terms of their origins such as animals including, for example, humans, canines, felines, mice, bovines, horses, rats, and chickens. However, such proteins or fragments thereof are preferably selected in view of compatibility with parent cells used for cell fusion. Mammal-derived proteins are generally preferable and human-derived proteins are particularly preferable. For instance, if the MCEMP1 is human MCEMP1, a human MCEMP1 protein, a partial polypeptide thereof, or cells capable of expressing human MCEMP1 can be used.

Nucleotide sequences and amino acid sequences of human MCEMP1 and homologs thereof can be obtained by, for example, accessing the website of GenBank (NCBI, USA) and using an algorithm such as BLAST or FASTA (Karlin and Altschul, Proc. Natl. Acad. Sci. USA, 90:5873-5877, 1993; Altschul et al., Nucleic Acids Res. 25:3389-3402, 1997).

According to the present invention, when the nucleotide sequence (SEQ ID NO: 1) or the amino acid sequence (SEQ ID NO: 2) of human MCEMP1 is used as a base sequence, targets are nucleic acids or proteins each consisting of a sequence having 70% to 100%, preferably 80% to 100%, more preferably 90% to 100%, and further preferably 95% to 100% (e.g., 97% to 100%, 98% to 100%, 99% to 100%, or 99.5% to 100%) sequence identity with the nucleotide sequence or amino acid sequence of the ORF or mature portion of the base nucleotide sequence or amino acid sequence. The term "% sequence identity" as used herein means a percentage (%) of the number of identical amino acids (or nucleotides) to the total number of amino acids (or nucleotides) in the case that two sequences are aligned such that maximum similarity can be achieved with or without introduction of gaps.

Fragments of an MCEMP1 protein have lengths ranging from the amino acid length of an epitope (or an antigenic determinant), which is the smallest unit of an antigen recognized by an antibody, to less than the full-length of the protein. The epitope refers to a polypeptide fragment having antigenicity or immunogenicity in mammals and preferably in humans. The smallest unit of the epitope consists of approximately 7 to 12 amino acids, and for example, 8 to 11 amino acids. A specific example thereof is a polypeptide consisting of the amino acid sequence having 80% or more, preferably 85% or more, more preferably 90% or more, and further preferably 95% or more sequence identity with the amino acid sequence of an MCEMP1 protein.

Polypeptides comprising the aforementioned human MCEMP1 protein and partial peptides thereof can be synthesized according to chemical synthesis methods such as the Fmoc method (fluorenylmethyloxycarbonyl method) or the tBoc method (t-butyloxycarbonyl method) (the Japanese Biochemical Society (ed.), "Biochemical Experimentation Course (Seikagaku Jikken Koza) 1," Protein Chemistry IV, Chemical Modification and Peptide Synthesis, Kagaku-dojin Publishing Company, Inc. (Japan), 1981). Also, they can be synthesized by general methods using a variety of commercially available peptide synthesizers. In addition, polypeptides of interest can be obtained by preparing polynucleotides encoding the above polypeptides, incorporating each of the polynucleotides into an expression vector and introducing the vector into a host cell, thereby allowing the host cell to produce the polypeptide, using known gene engineering methods (Sambrook et al., Molecular Cloning, 2nd edition, Current Protocols in Molecular Biology (1989), Cold Spring Harbor Laboratory Press; Ausubel et al., Short Protocols in Molecular Biology, 3rd edition, A Compendium of Methods from Current Protocols in Molecular Biology (1995), John Wiley & Sons, etc.).

Polynucleotides encoding the aforementioned polypeptides can be readily prepared by known gene engineering techniques or general methods using commercially available nucleic acid synthesizers. For example, DNA comprising the nucleotide sequence shown in SEQ ID NO: 1 can be prepared by PCR using a human chromosome DNA or cDNA library as a template and a pair of primers designed to enable the amplification of the nucleotide sequence shown in SEQ ID NO: 1. PCR conditions can be appropriately determined. For example, such conditions may comprise conducting 30 cycles of the reaction steps (as one cycle) consisting of: 94° C., 30 seconds (denaturation); 55° C., 30 seconds to 1 minute (annealing); and 72° C., 1 minute (elongation) using a thermostable DNA polymerase (e.g., Taq polymerase) and a $Mg^{2+}$-containing PCR buffer, followed by reaction at 72° C. for 7 minutes after completion of the 30 cycles. However, PCR conditions are not limited to the above-exemplified PCR conditions. PCR techniques and conditions are described in, for example, Ausubel et al., Short Protocols in Molecular Biology, 3rd edition, A Compendium of Methods from Current Protocols in Molecular Biology (1995), John Wiley & Sons (Chapter 15, in particular).

In addition, desired DNA can be isolated by preparing appropriate probes and primers based on information about the nucleotide and amino acid sequences shown in SEQ ID NOS: 1 to 8 in the Sequence Listing of the application, and screening a cDNA library of e.g. human with the use of such probes and primers. Preferably, such cDNA library is produced from a cell, organ, or tissue in which the protein with SEQ ID NO: 2, 4, 6 or 8 is expressed. Examples of the cell or tissue include, but not limited to, cells or tissues from cancers or tumors, such as bone marrow, peripheral blood mononuclear cell (PBMC), leukemia, myelodysplastic syndrome, osteosarcoma, thymoma, mastocytoma, and perianal adenocarcinoma. Operations such as preparation of probes or primers, construction of cDNA libraries, screening of cDNA libraries, and cloning of genes of interest, as described above, are known to persons skilled in the art, and they can be carried out according to, for example, the methods described in Sambrook et al., Molecular Cloning, the 2nd edition, Current Protocols in Molecular Biology (1989) and Ausbel et al. (ibid.). DNAs encoding human MCEMP1 protein and partial peptides thereof can be obtained from the thus obtained DNAs.

The above-described host cells may be any cells, as long as they can express the above-described polypeptides. An example of prokaryotic host cell includes, but is not limited to, *Escherichia coli*. Examples of eukaryotic host cells include, but are not limited to, mammalian cells such as monkey kidney cell (COS1), Chinese hamster ovary cell (CHO), human embryonic kidney cell line (HEK293), and mouse embryonic skin cell line (NIH3T3), yeast cells such as budding yeast and fission yeast cells, silkworm cells, and *Xenopus laevis* egg cells.

When prokaryotic cells are used as host cells, an expression vector preferably having an origin replicable in prokaryotic cells, a promoter, a ribosome-binding site, a multicloning site, a terminator, a drug resistance gene, an auxotrophic complementary gene, a reporter gene, or the like can be used. As expression vectors for *Escherichia coli*, pUC vectors, pBluescriptII, pET expression systems, pGEX expression systems, and the like can be exemplified. A DNA encoding the above polypeptide is incorporated into such an expression vector, a prokaryotic host cell is transformed with the vector, and then the thus obtained transformed cell is cultured, so that the polypeptide encoded by the DNA can be expressed in the prokaryotic host cell. At this time, the polypeptide can also be expressed as a fusion protein with another protein.

When eukaryotic cells are used as host cells, expression vectors for eukaryotic cells preferably having a promoter, a splicing region, a poly(A) addition site, or the like can be used. Examples of such expression vectors include pKA1, pCDM8, pSVK3, pMSG, pSVL, pBK-CMV, pBK-RSV, EBV vector, pRS, pcDNA3.1, pSecTag (A, B, C) and pYES2. By similar procedures to those mentioned above, a DNA encoding the aforementioned polypeptide is incorporated into such an expression vector, an eukaryotic host cell is transformed with the vector, and then the thus obtained transformed cell is cultured, so that the polypeptide encoded by the above DNA can be expressed in the eukaryotic host cell. When pIND/V5-His, pFLAG-CMV-2, pEGFP-N1, pEGFP-C1, or the like is used as an expression vector, the above polypeptide may be expressed as a fusion protein with a tag, such as His tag (e.g., (His)6 to (His)10), FLAG tag, myc tag, HA tag, or GFP.

For introduction of an expression vector into a host cell, well known methods can be employed, such as electroporation, a calcium phosphate method, a liposome method, a DEAE dextran method, microinjection, viral infection, lipofection, and binding with a cell-membrane-permeable peptide.

Isolation and purification of a polypeptide of interest from host cells can be performed using known isolation techniques in combination. Examples of isolation and purification techniques include, but are not limited to, treatment using a denaturing agent such as urea or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion exchange chromatography, hydrophobic chromatography, affinity chromatography, and reverse phase chromatography.

<Structure of Antibody>

In general, antibodies are heteromultimeric glycoproteins each comprising at least two heavy chains and two light chains. Meanwhile, another class of antibodies except for IgM are heterotetrameric glycoproteins (approximately 150 kDa) each comprising two identical light (L) chains and two identical heavy (H) chains. Typically, each light chain is connected to a heavy chain via a single covalent disulfide bond. However, the number of disulfide bonds between heavy chains varies among different immunoglobulin isotypes. Each of heavy chain and light chain also has an intrachain disulfide bond(s). Each heavy chain has a variable domain (VH region) at one end thereof, to which some constant regions are bound in series. Each light chain has a variable domain (VL region) at one end thereof and has a single constant region at the opposite end thereof. The constant region of a light chain is aligned with the first constant region of a heavy chain and the light-chain variable domain is aligned with the heavy-chain variable domain. A specific region of an antibody variable domain, which is called "complementarity determining region (CDR)," exhibits its specific variability so as to impart binding specificity to an antibody. A relatively conserved portion in a variable region is called a "framework region (FR)." A complete heavy-chain or light-chain variable domain comprises 4 FRs connected to each other via 3 CDRs. Such CDRs are called "CDRH1," "CDRH2," and "CDRH3," respectively, in such order from the N-terminus in a heavy chain. Similarly, for a light chain, they are called "CDRL1," "CDRL2," and "CDRL3," respectively. CDRH3 plays the most important role in terms of antibody-antigen binding specificity. In addition, CDRs in each chain are retained by FR regions in the state that they are close to each other, and they contribute to the formation of antigen binding sites of an antibody together with CDRs in a corresponding chain. Constant regions do not directly contribute to antibody-antigen binding. However, they exhibit various effector functions such as association with antibody-dependent cytotoxicity (ADCC activity), phagocytosis through binding to an Fcγ receptor, half-life/clearance rate via a neonatal Fc receptor (FcRn), and complement-dependent cytotoxicity (CDC activity) via a C1q component in the complement cascade.

<Antibody Production>

The term "anti-MCEMP1 antibody" used in the present invention refers to an antibody having an immunological reactivity with a full-length MCEMP1 protein or a fragment thereof described above.

The term "immunological reactivity" used herein indicates the characteristics of an antibody binding in vivo or in vitro to an MCEMP1 antigen. The tumor- or tumor cell-damaging function (e.g., death, inhibition, or regression) can be expressed as a result of such binding. Specifically, any type of antibody may be used in the present invention as long as the antibody can bind to an MCEMP1 protein to damage a tumor, preferably a cancer expressing (or having) the MCEMP1 protein on a cell surface, such as leukemia, myelodysplastic syndrome, osteosarcoma, thymoma, mastocytoma, or perianal adenocarcinoma.

Examples of such antibodies include monoclonal antibodies, polyclonal antibodies, synthetic antibodies, multispecific antibodies (e.g., bispecific antibodies), human antibodies, humanized antibodies, chimeric antibodies, and single-chain antibodies. Examples of such antibodies also include antibody fragments (e.g., fragments such as Fab and F(ab')

$_2$). In addition, antibodies may be any class of immunoglobulin molecules such as IgG, IgE, IgM, IgA, IgD, and IgY, or any subclass thereof such as IgG1, IgG2, IgG3, IgG4, IgA1, and IgA2.

Antibodies may be further modified via acetylation, formylation, amidation, phosphorylation, or pegylation (PEG), in addition to glycosylation.

Production examples for a variety of antibodies are described below.

The polyclonal antibodies that can be used in the present invention can be obtained in a manner described below.

Serum is obtained by immunizing small animals such as mice, human antibody-producing mice, or rabbits with a naturally occurring MCEMP1 protein, a recombinant MCEMP1 protein that has been expressed as a protein fused with GST or the like in a microorganism such as *Escherichia coli*, or a partial peptide thereof. The serum is purified via ammonium sulfate precipitation, protein A/protein G column chromatography, DEAE ion-exchange chromatography, affinity column chromatography with a column to which an MCEMP1 protein or a synthetic peptide is coupled, or the like for preparation of polyclonal antibodies. In the Examples described below, a mouse polyclonal antibody against a domain expressed on cancer cell surfaces in an MCEMP1 protein amino acid sequence was produced, and antitumor effects thereof were confirmed.

Other examples of the antibodies that can be used in the present invention include monoclonal antibodies. For example, monoclonal antibodies can be obtained in a manner described below. For example, cells expressing the MCEMP1 protein on their surfaces (such as a leukemia cell line U937 or the like) is administered to mice for immunization, followed by extraction of spleens from the mice. Cells are separated from each spleen and then are fused with mouse myeloma cells. Clones capable of producing an antibody having cancer cell growth inhibition action are selected from the obtained fusion cells (hybridomas). A monoclonal antibody-producing hybridoma having cancer cell growth inhibition action is isolated and cultured. An antibody of interest can be prepared via purification from the culture supernatant by a general affinity purification method.

Also, a monoclonal antibody-producing hybridoma can be produced in a manner described below, for example. First, an animal is immunized with a sensitizing antigen by a known method. In a general method, immunization is carried out by intraperitoneally or subcutaneously injecting a sensitizing antigen into a mammal. Specifically, a sensitizing antigen is diluted with or suspended in PBS (Phosphate-Buffered Saline), physiological saline, or the like to an appropriate resultant amount. If desired, an appropriate amount of a conventional adjuvant (e.g., Freund's complete adjuvant) is mixed therewith. After emulsification takes place, the resultant is administered to a mammal several times every 4 to 21 days. In addition, an adequate carrier can be used for immunization with a sensitizing antigen.

As described above, after immunization of a mammal and confirmation of an increase to a desired antibody level in serum, immunocytes are collected from the mammal and subjected to cell fusion. Particularly preferable examples of immunocytes are splenocytes.

Mammalian myeloma cells are used as relevant parent cells subjected to fusion with the above immunocytes. For such myeloma cells, the following various examples of known cell lines are preferably used: P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976). 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S. J. Exp. Med. (1978) 148, 313-323), and R210 (Galfre, G. et al., Nature (1979) 277, 131-133).

Basically, cell fusion of immunocytes and myeloma cells described above can be carried out according to a known method such as the method of Kohler and Milstein et al. (Kohler, G. and Milstein, C. Methods Enzymol. (1981) 73, 3-46).

More specifically, cell fusion described above is carried out, for example, in the presence of a cell fusion promoter in a conventional nutrients-containing culture solution. Examples of a fusion promoter to be used include polyethylene glycol (PEG) and Sendai virus (HVJ: hemagglutinating virus of Japan). If desired, an adjuvant such as dimethylsulfoxide may be further added for improvement of fusion efficiency.

The proportion of immunocytes used to that of myeloma cells used can be arbitrarily determined. For example, the ratio of immunocytes to myeloma cells is preferably 1:1 to 10:1. Examples of a culture solution that can be used for cell fusion described above include an RPMI1640 culture solution and an MEM culture solution adequate for growth of the above myeloma cell lines as well as other conventional culture solutions used for this kind of cell culture. Further, a serum replacement such as fetal calf serum (FCS) can be used in combination therewith.

For cell fusion, the above immunocytes and myeloma cells are sufficiently mixed at predetermined amounts in the culture solution. A PEG solution (e.g., average molecular weight: approximately 1000 to 6000) that has been previously heated to approximately 37° C. is added thereto at a concentration of generally 30% to 60% (w/v), followed by mixing. This results in formation of hybridomas of interest. Subsequently, sequential addition of an appropriate culture solution and removal of the supernatant via centrifugation are repeatedly carried out to remove cell fusion agent(s) and the like that are not preferable for the growth of hybridomas.

The thus obtained hybridomas are cultured in a conventional selection culture solution such as an HAT culture solution (a culture solution comprising hypoxanthine, aminopterin, and thymidine) for selection. Culture in such an HAT culture solution is continuously carried out for a sufficient time period (generally several days to several weeks) for death of cells (non-fused cells) other than hybridomas of interest. Next, a conventional limiting dilution method is employed to screen for hybridomas producing antibodies of interest and to carry out single cloning.

Further, as well as obtaining the above hybridomas via immunization of non-human animals with antigens, it is also possible to obtain hybridomas that produce human antibodies having a desired activity (e.g., cell growth inhibition activity) by sensitizing human lymphocytes (e.g., human lymphocytes infected with EB virus) in vitro with a protein, protein-expressing cells, or a lysate thereof and fusing the sensitized lymphocytes with human-derived myeloma cells having the ability to permanently divide (e.g., U266) (accession no. TIB196).

Monoclonal antibody-producing hybridomas produced as above can be passaged in a conventional culture solution. In addition, they can be preserved in liquid nitrogen for a long period of time.

Specifically, immunization is carried out using a desired antigen or cells expressing a desired antigen as sensitizing antigen(s) according to a conventional immunization method. The obtained immunocytes are fused with known parent cells by a conventional cell fusion method. Then, monoclonal antibody-producing cells (hybridomas) are screened for by a conventional screening method. Thus, antibody production can be carried out.

A known human antibody-producing mouse used herein is, for example, a KM Mouse (Kirin Pharma/Medarex) or a XenoMouse (Amgen) (e.g., WO02/43478 and WO02/092812). When such mice are immunized with MCEMP1 proteins or fragments thereof, complete human polyclonal antibodies can be obtained from blood. In addition, complete human monoclonal antibodies can be produced by a method of fusing splenocytes collected from immunized mice with myeloma cells.

Antigen preparation can be carried out in accordance with a method such as a method using animal cells (JP Patent Publication (Kohyo) No. 2007-530068) or a method using a baculovirus (e.g., WO98/46777). If the immunogenicity of an antigen is low, an antigen is bound to a macromolecule having immunogenicity, such as albumin. Then, the antigen can be used for immunization.

Further, it is possible to use a gene recombinant antibody produced by cloning an antibody gene from a hybridoma, incorporating the clone into an adequate vector, introducing the vector into a host, and using a genetic engineering technique. (See, for example, Carl, A. K. Borrebaeck, James, W. Larrick, THERAPEUTIC MONOCLONAL ANTIBODIES, Published in the United Kingdom by MACMILLAN PUBLISHERS LTD, 1990.) Specifically, cDNA of a variable region (V region) of an antibody is synthesized from mRNA of a hybridoma with the use of a reverse transcriptase. After DNA encoding a V region of an antibody of interest is obtained, such DNA is ligated to desired DNA encoding an antibody constant region (C region). The resultant is incorporated into an expression vector. Alternatively, DNA encoding an antibody V region may be incorporated into an expression vector comprising DNA of an antibody C region. Such DNA is incorporated into an expression vector in a manner such that it is expressed under control of an expression control region such as an enhancer or a promoter. Next, host cells are transformed with such expression vector, thereby allowing the antibody to be expressed.

Monoclonal antibodies include human monoclonal antibodies and non-human animal monoclonal antibodies (e.g., mouse monoclonal antibodies, rat monoclonal antibodies, rabbit monoclonal antibodies, and chicken monoclonal antibodies). Monoclonal antibodies can be produced by culturing hybridomas obtained via fusion of myeloma cells and splenocytes from non-human mammals (e.g., mice or human antibody-producing mice) immunized with MCEMP1 proteins or fragments thereof.

A chimeric antibody is an antibody produced by combining sequences from different animals. An example thereof is an antibody consisting of mouse antibody heavy-chain and light-chain variable regions and human antibody heavy-chain and light-chain constant regions. Such a chimeric antibody can be produced by a known method. For example, a chimeric antibody can be obtained by ligating DNA encoding an antibody V region to DNA encoding a human antibody C region, incorporating the resultant into an expression vector, introducing the vector into a host, and allowing the host to produce an antibody.

Polyclonal antibodies include antibodies obtained by immunizing human antibody-producing animals (e.g., mice) with MCEMP1 proteins or fragments thereof.

A humanized antibody is an engineered antibody, and it is sometimes referred to as a "reshaped human antibody." A humanized antibody is constructed by transplanting CDRs of an immunized animal-derived antibody into complementarity determining regions of a human antibody. Also, general genetic engineering techniques therefor are known.

Specifically, a DNA sequence designed to ligate mouse antibody CDRs to framework regions (FRs) of a human antibody is synthesized by PCR method using several oligonucleotides prepared to have portions overlapping each other at their ends. A humanized antibody can be obtained by ligating the above obtained DNA to DNA encoding a human antibody constant region, incorporating the resultant into an expression vector, introducing the vector into a host, and allowing the host to produce an antibody production (see EP-A-239400 and WO96/02576). Human antibody FRs to be ligated to each other via CDRs are selected, provided that complementarity determining regions can form a good antigen binding site. If necessary, amino acids in framework regions of an antibody variable region may be substituted in such a manner that complementarity determining regions in a reshaped human antibody form an appropriate antigen binding site (Sato K. et al., Cancer Research 1993, 53: 851-856). In addition, the framework regions may be substituted with framework regions from various human antibodies (see WO99/51743).

After a chimeric antibody or a humanized antibody is produced, amino acids in a variable region (e.g., FR) or a constant region may be, for example, substituted with different amino acids.

Here, the amino acid substitution is a substitution of, for example, less than 15, less than 10, not more than 8, not more than 7, not more than 6, not more than 5, not more than 4, not more than 3, or not more than 2 amino acids, preferably 1 to 5 amino acids, and more preferably 1 or 2 amino acids. A substituted antibody should be functionally equivalent to an unsubstituted antibody. The substitution is preferably a conservative amino acid substitution, which is a substitution between amino acids having similar characteristics in terms of charge, side chains, polarity, aromaticity, and the like. For example, amino acids having similar characteristics can be classified into the following types: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched-chain amino acids (threonine, valine, isoleucine); and aromatic amino acids (phenylalanine, tyrosine, tryptophan, and histidine).

Antibodies of the present invention may be modified antibodies. An example of a modified antibody is an antibody bound to a molecule such as polyethylene glycol (PEG). Regarding modified antibody of the present invention, substances that bind to an antibody are not limited. Such a modified antibody can be obtained by chemically modifying an obtained antibody. A method of such modification has been already established in the field related to the present invention.

The expression "functionally equivalent" used herein indicates a situation in which an antibody of interest has biological or biochemical activity similar to that of an antibody of the present invention. Specifically, such antibody has a function of damaging tumors and causes essentially no rejection reaction when applied to humans. An example of such activity is cell growth inhibition activity or binding activity.

A known method for preparing a polypeptide functionally equivalent to a given polypeptide that is well known to persons skilled in the art is a method comprising introducing a mutation into a polypeptide. For instance, a person skilled in the art can adequately introduce a mutation into an antibody of the present invention using a site-specific mutagenesis method (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; or Kunkel (1988) Methods Enzymol. 85, 2763-2766) or the like. Thus, an antibody functionally equivalent to the antibody of the present invention can be prepared.

An aforementioned antibody capable of recognizing an epitope of an MCEMP1 protein recognized by an anti-MCEMP1 antibody can be obtained by a method known to persons skilled in the art. For example, it can be obtained by: a method comprising determining an epitope of an MCEMP1 protein recognized by an anti-MCEMP1 antibody by a general method (e.g., epitope mapping) and producing an antibody using a polypeptide having an amino acid sequence contained in the epitope as an immunogen; or a method comprising determining an epitope of a produced antibody by a general method and selecting an antibody having an epitope identical to an epitope of an anti-MCEMP1 antibody. Here, the term "epitope" refers to a polypeptide fragment having antigenicity or immunogenicity in mammals and preferably in humans. The smallest unit thereof consists of approximately 7 to 12 amino acids and preferably 8 to 11 amino acids.

The affinity constant Ka (kon/koff) of an antibody of the present invention is preferably at least $10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, or at least $10^{13}$ M$^{-1}$.

An antibody of the present invention can be conjugated with an antitumor agent. Binding between an antibody and an antitumor agent can be carried out via a spacer having a group reactive to an amino group, a carboxyl group, a hydroxy group, a thiol group, or the like (e.g., an imidyl succinate group, a formyl group, a 2-pyridyldithio group, a maleimidyl group, an alkoxycarbonyl group, or a hydroxy group).

Examples of antitumor agents include the following antitumor agents known in references or the like: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRIAMYCIN, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof.

Alternatively, it is also possible to bind a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu, or $^{176}$Lu known in references and the like to an antibody of the present invention. It is desirable for such radioactive isotopes to be effective for tumor treatment or diagnosis.

An antibody of the present invention is preferably an antibody having an immunological reactivity with MCEMP1 or an antibody capable of specifically recognizing MCEMP1 Such an antibody should be an antibody having a structure that allows a subject animal to which the antibody is administered to completely or almost completely avoid a rejection reaction. If the subject animal is a human, examples of such antibodies include human antibodies, humanized antibodies, chimeric antibodies (e.g., human-mouse chimeric antibodies), single-chain antibodies, and bispecific antibodies. Such an antibody is a recombinant antibody having human antibody-derived heavy-chain and light-chain variable regions, a recombinant antibody having heavy-chain and light-chain variable regions each consisting of non-human animal antibody-derived complementarity determining regions (CDR1, CDR2, and CDR3) and human antibody-derived framework regions, or a recombinant antibody having non-human animal antibody-derived heavy-chain and light-chain variable regions and human antibody-derived heavy-chain and light-chain constant regions. The first two antibodies are preferable.

The above recombinant antibody can be produced in the manner described below. DNA encoding a monoclonal antibody against human MCEMP1 (e.g., a human monoclonal antibody, a mouse monoclonal antibody, a rat monoclonal antibody, a rabbit monoclonal antibody, or a chicken monoclonal antibody) is cloned from an antibody-producing cell such as a hybridoma. DNAs encoding a light-chain variable region and a heavy-chain variable region of the antibody are produced by an RT-PCR method or the like using the obtained clone as a template. Then, the sequences of a light-chain variable region and a heavy-chain variable region or the sequences of CDR1, CDR2, and CDR3 are determined by the Kabat EU numbering system (Kabat et al., Sequences of Proteins of Immunological Interest, 5th Ed. Public Health Service, National Institute of Health, Bethesda, Md. (1991)).

Further, such DNAs encoding variable regions or DNAs encoding CDRs are produced by a genetic engineering technique (Sambrook et al., Molecular Cloning A Laboratory Manual, Cold Spring Harbor Laboratory Press (1989)) or a DNA synthesizer. Here, the above human monoclonal antibody-producing hybridoma can be produced by immunizing a human antibody-producing animal (e.g., a mouse) with human MCEMP1 and fusing splenocytes from the spleen removed from the animal with myeloma cells. In addition to the above, if necessary, DNAs encoding human antibody-derived light-chain or heavy-chain variable regions and constant regions are produced by a genetic engineering technique or a DNA synthesizer.

In the case of a humanized antibody, DNA in which the CDR coding sequences in a DNA encoding a human antibody-derived light-chain or heavy-chain variable region have been substituted with corresponding CDR coding sequences of an antibody from a non-human animal (e.g., a mouse, a rat, or a chicken) is produced. The DNA obtained as above is ligated to the DNA encoding a constant region of a human antibody-derived light chain or heavy chain. Thus, DNA encoding a humanized antibody can be produced.

In the case of a chimeric antibody, DNA encoding an antibody light-chain or heavy-chain variable region from a non-human animal (e.g., a mouse, a rat, or a chicken) is ligated to the DNA encoding a human antibody-derived light-chain or heavy-chain constant region. Thus, DNA encoding a chimeric antibody can be produced.

A single-chain antibody is an antibody in which a heavy-chain variable region and a light-chain variable region are linearly ligated to each other via a linker. DNA encoding a single-chain antibody can be produced by ligating DNA encoding a heavy-chain variable region, DNA encoding a linker, and a DNA encoding a light-chain variable region together. Here, a heavy-chain variable region and a light-chain variable region are those from a human antibody or those from a human antibody in which CDRs alone have been substituted with CDRs of an antibody from a non-human animal (e.g., a mouse, a rat, or a chicken). In addition, the linker consists of 12 to 19 amino acids. An example thereof is (G4S)3 consisting of 15 amino acids (G. B. Kim et al., Protein Engineering Design and Selection 2007, 20 (9): 425-432).

A bispecific antibody (diabody) is an antibody capable of specifically binding to two different epitopes. DNA encoding a bispecific antibody can be produced by, for example, ligating DNA encoding a heavy-chain variable region A, DNA encoding a light-chain variable region B, DNA encoding a heavy-chain variable region B, and DNA encoding a light-chain variable region A together in such order (provided that DNA encoding a light-chain variable region B and DNA encoding a heavy-chain variable region B are ligated to each other via DNA encoding a linker described above). Here, both a heavy-chain variable region and a light-chain variable region are those from a human antibody or those from a human antibody in which CDRs alone have been substituted with CDRs of an antibody from a non-human animal (e.g., a mouse, a rat, or a chicken).

Recombinant DNA produced as above is incorporated into one or a plurality of appropriate vector(s). Each such vector is introduced into a host cell (e.g., a mammal cell, a yeast cell, or an insect cell) for (co)expression. Thus, a recombinant antibody can be produced. See, P. J. Delves, ANTIBODY PRODUCTION ESSENTIAL TECHNIQUES, 1997 WILEY, P. Shepherd and C. Dean, Monoclonal Antibodies, 2000 OXFORD UNIVERSITY PRESS; J. W. Goding, Monoclonal Antibodies: Principles and Practice, 1993 ACADEMIC PRESS.

The above antibodies preferably have cytotoxic activity, thereby exhibiting antitumor effects.

In addition, a hybridoma capable of producing a different human antibody or a non-human animal antibody (e.g., a mouse antibody) against human MCEMP1 is produced. A monoclonal antibody produced by the hybridoma is collected. Then, it is determined whether or not the obtained antibody is an antibody of interest using, as indicators, immunological binding activity to human MCEMP1 and cytotoxic activity. Thus, a monoclonal antibody-producing hybridoma of interest is identified. Thereafter, as described above, DNAs encoding heavy-chain and light-chain variable regions of an antibody of interest are produced from the hybridoma and sequenced. The DNAs are used for production of different antibodies.

Further, the above antibody of the present invention may be any one of antibodies having a substitution, deletion, or addition of one or several (and preferably, 1 or 2) amino acid(s), particularly in a framework region sequence and/or a constant region sequence, as long as it has the specific property of specifically recognizing MCEMP1. Here, the term "several amino acids" indicates 2 to 5 and preferably 2 or 3 amino acids.

Furthermore, according to the present invention, DNA encoding the above antibody of the present invention, DNA encoding a heavy chain or light chain of the antibody, or DNA encoding a heavy-chain or light-chain variable region of the antibody is also provided.

Complementarity determining regions (CDRs) encoded by DNAs of the above sequences are regions that determine antibody specificity. Therefore, sequences encoding the other regions (i.e., constant regions and framework regions) in an antibody may be sequences from a different antibody. Here, different antibodies include antibodies from non-human organisms. However, in view of reduction of side effects, human-derived antibodies are preferable. That is to say, in the above case, DNA regions encoding framework regions and constant regions of heavy and light chains preferably comprise nucleotide sequences encoding the relevant amino acid sequences from a human antibody.

DNA of the present invention can be obtained by, for example, the aforementioned methods or the following methods. First, total RNA is prepared from a hybridoma for an antibody of the present invention using a commercially available RNA extraction kit. Then, cDNA is synthesized with a reverse transcriptase using random primers and the like. Next, cDNA encoding an antibody is amplified by a PCR method using, as primers, oligonucleotides having sequences conserved in variable regions of known mouse antibody heavy-chain and light-chain genes. Sequences encoding constant regions can be obtained by amplifying known sequences by a PCR method. The nucleotide sequence of the DNA can be determined by a general method involving, for example, incorporation into a plasmid or phage for sequence determination.

It is thought that antitumor effects of an anti-MCEMP1 antibody used in the present invention upon MCEMP1-expressing cancer cells are exhibited through effector cell-mediated antibody-dependent cellular cytotoxicity (ADCC) activity against MCEMP1-expressing cells or complement-dependent cytotoxicity (CDC) activity against MCEMP1-expressing cells.

Accordingly, the activity of an anti-MCEMP1 antibody used in the present invention can be evaluated via in vitro determination of ADCC activity or CDC activity to MCEMP1-expressing cancer cells as specifically described in the Examples mentioned below.

An anti-MCEMP1 antibody used in the present invention binds to a MCEMP1-protein on a cancer cell and exhibits antitumor effects based on the above activity. Therefore, such antibody is believed to be useful for cancer treatment or prevention. Specifically, according to the present invention, a pharmaceutical composition for treatment and/or prevention of cancer that comprises, as an active ingredient, an anti-MCEMP1 antibody, is provided. When an anti-MCEMP1 antibody is used for the purpose of administering the antibody to humans (antibody treatment), it is preferably used in the form of a human antibody or a humanized antibody in order to reduce immunogenicity.

In addition, as the binding affinity between an anti-MCEMP1 antibody and an MCEMP1 protein on a cancer cell surface becomes higher, stronger antitumor activity can be exhibited by an anti-MCEMP1 antibody. Therefore, if an anti-MCEMP1 antibody having high binding affinity to an MCEMP1 protein can be obtained, even stronger antitumor effects can be expected to be exhibited. Accordingly, it becomes possible to use such antibody as a pharmaceutical composition for treatment and/or prevention of cancer. As described above, for high binding affinity, the affinity constant Ka (kon/koff) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

<Binding to Antigen Expression Cells>

The capacity of an antibody to bind to MCEMP1 can be determined via binding assay using, for example, ELISA, a Western blot method, immunofluorescence, or flowcytometry analysis as described in the Examples.

<Immunohistochemical Staining>

An antibody that recognizes MCEMP1 can be tested in terms of reactivity with MCEMP1 by an immunohistochemical method well-known to persons skilled in the art using a frozen tissue section fixed with paraformaldehyde or acetone or a paraffin-embedded tissue section fixed with paraformaldehyde. Such section is prepared from a tissue obtained from a patient during surgery, a bone marrow tissue, lymph node, or peripheral blood cells of a patient, or a tissue obtained from an animal carrying xenograft tissue that has been inoculated with a cell line that expresses MCEMP1 naturally or after transfection thereof.

For immunohistochemical staining, an antibody immunologically reactive to MCEMP1 can be stained by a variety of methods. For example, it can be visualized by reacting with a horseradish peroxidase-conjugated goat anti-mouse antibody or goat anti-rabbit antibody.

<Pharmaceutical Composition>

The present invention provides a pharmaceutical composition (or medicament) comprising an antibody of the present invention, i.e., an antibody against MCEMP1 or fragment (preferably antigen binding fragment) thereof described above. The pharmaceutical composition (or medicament) of the present invention usually comprises an effective amount of the antibody against MCEMP1 or fragment (preferably antigen binding fragment) thereof described above.

A target of the pharmaceutical composition for treatment and/or prevention of a cancer of the present invention is not particularly limited as long as the target is a cancer (cell) expressing the MCEMP1 gene.

Both the terms "tumor" and "cancer" used herein refer to malignant neoplasm, and thus they are used in an exchangeable manner.

A cancer that can be a target in the present invention is a cancer expressing a gene encoding a polypeptide comprising an amino acid sequence of SEQ ID NO: 2, 4, 6, or 8 or a partial sequence consisting of 7 or more consecutive amino acids of said amino acid sequence, and is preferably a cancer expressing such a polypeptide on a cell surface. The cancer that can be a target in the present invention is preferably leukemia, myelodysplastic syndrome, osteosarcoma, thymoma, mastocytoma, or perianal adenocarcinoma. Examples of these specific cancers include, but are not limited to, acute non-lymphocytic leukemia, chronic lymphocytic leukemia, acute granulocytic leukemia, chronic granulocytic leukemia, acute promyelocytic leukemia, adult T-cell leukemia, aleukemic leukemia, leukocythemic leukemia, basophilic leukemia, blastic leukemia, bovine leukemia, chronic myeloleukemia, leukemia cutis, embryonal leukemia, eosinophilic leukemia, Gross leukemia, Rieder cell leukemia, Schilling's leukemia, stem cell leukemia, subleukemic leukemia, undifferentiated cell leukemia, hairy cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphotropic leukemia, lymphoid leukemia, lymphosarcoma cell leukemia, mast cell leukemia, megakaryocytic leukemia, micromyeloblastic leukemia, monocytic leukemia, myeloblastic leukemia, myeloleukemia, myeloid granulocytic leukemia, myelomonocytic leukemia, Naegeli leukemia, plasma cell leukemia, plasmacytic leukemia, promyelocytic leukemia, refractory anemia (RA), refractory anemia with ringed sideroblasts (RARS), refractory anemia with excess blasts (RAEB), RAEB in transformation (RAEB-T), preleukemia and chronic myelomonocytic leukemia (CMML), conventional central osteosarcoma and subtypes of osteosarcoma (intraosseous well-differentiated osteosarcoma, round cell osteosarcoma, surface osteosarcoma, parosteal osteosarcoma, periosteal osteosarcoma and high-grade surface osteosarcoma), thymoma, mastocytoma, perianal adenoma, and perianal adenocarcinoma.

In addition, the subject animal of the present invention is a mammal. Examples thereof include mammals such as primates, pet animals, livestock animals, sport animals, and experimental animals. Humans, dogs, and cats are particularly preferable.

When an antibody used in the present invention is used as a pharmaceutical composition, it can be formulated by a method known to persons skilled in the art. For instance, it can be parenterally used in the form of a parenteral injection of: an aseptic solution comprising water or a pharmacologically acceptable non-water solution; or a suspension liquid. For example, in one possible case, it can be formulated with the combined use of a pharmacologically acceptable carrier or medium or additive and specifically sterilized water, physiological saline, plant oil, an emulsifier, a suspension, a surfactant, a stabilizer, a flavoring agent, an excipient, a vehicle, a preservative, or a binder in an appropriate manner by mixing in a unit dosage form required for a generally acceptable pharmaceutical formulation. The amount of an active ingredient in a formulation is determined such that an appropriate dosage within the indicated range can be achieved.

An aseptic composition for injection purposes can be formulated in accordance with general formulation practice using a vehicle such as distilled water for injection purposes.

Examples of an aqueous solution for injection purposes include physiological saline and isotonic solutions comprising glucose and other adjuvants such as D-sorbitol, D-mannose, D-mannitol, and sodium chloride. Such solution may be used with an appropriate dissolution aid. Examples of such dissolution aid include alcohols such as ethanol and polyalcohol, propylene glycol, polyethylene glycol, and nonion surfactants such as polysorbate 80™ and HCO-60.

Examples of oily liquid include sesame oil and soybean oil. Such oily liquid may be used in combination with a dissolution aid such as benzyl benzoate or benzyl alcohol. In addition, it may be mixed with a buffering agent such as a phosphate buffer solution, a sodium acetate buffer solution, a soothing agent such as procaine hydrochloride, a stabilizer such as benzyl alcohol, phenol, or an antioxidant. In general, a formulated injection solution is introduced into an adequate ample.

The above pharmaceutical composition is orally or parenterally administered. Preferably, it is parenterally administered. Specific examples of dosage forms include injectable dosage form, intranasally-administered dosage form, transpulmonarily-administered dosage form, and percutaneously-administered dosage form. For example, injectable dosage form can be systemically or locally administered via intravenous injection, intramuscular injection, intraperitoneal injection, or subcutaneous injection. Alternatively, an antibody of the present invention may be administered directly to a tumor by local administration, such as injection, infusion, or implantation of a sustained-release formation, to the tumor.

In addition, the administration method can be appropriately determined depending on patient age, weight, gender, and symptoms. A single dose of a pharmaceutical composition comprising an antibody or a polynucleotide encoding an antibody can be selected within a range of, for example, 0.0001 mg to 1000 mg per kg of body weight. Alternatively, the dose can be selected within a range of, for example, 0.001 to 100000 mg per patient's body; however, it is not necessarily limited thereto. The dose and the administration method are changed depending on patient age, weight, gender, and symptoms. However, persons skilled in the art can appropriately select the dose and the method.

The cancer described above, particularly, a cancer expressing MCEMP1 on a cell surface, preferably leukemia, myelodysplastic syndrome, osteosarcoma, thymoma, mastocytoma, or perianal adenocarcinoma can be treated and/or prevented by administering an antibody of the present invention or fragment thereof, or the pharmaceutical composition comprising the same to a subject.

Further, a method for treating and/or preventing a cancer, which comprises administering, to a subject, the pharmaceutical composition (or medicament) of the present invention in combination with an antitumor agent as listed above or a pharmaceutical composition (or medicament) comprising the antitumor agent, is also included in the present invention. A target cancer is the same as above. The antibody or fragment thereof according to the present invention and the antitumor agent can be administered concurrently or separately to the subject. In the case of separately administering them, either of the pharmaceutical compositions can be administered first or later, and their dosing intervals, doses, administration routes, and the number of doses can be appropriately selected by a specialist physician. In the case of concurrently administering them, for example, a pharmaceutical composition in a dosage form obtained by mixing the antibody or fragment thereof according to the present invention and the antitumor agent in a pharmacologically acceptable carrier (or medium) for formulation is also included in the present invention. The description about prescription, formulation, administration routes, doses, cancers, etc. regarding pharmaceutical compositions and dosage forms containing antibodies of the present invention is applicable to all of the pharmaceutical compositions and dosage forms containing antitumor agents.

Accordingly, the present invention also provides a pharmaceutical combination for treatment and/or prevention of a cancer, which comprises the pharmaceutical composition of the present invention and a pharmaceutical composition comprising an antitumor agent as listed above, and a method for treating and/or preventing a cancer, which comprises administering the same. In addition, the present invention also provides a pharmaceutical composition for treatment and/or prevention of a cancer, which comprises an antibody of the present invention or fragment thereof and an antitumor agent together with a pharmacologically acceptable carrier and/or additive.

EXAMPLES

The present invention is hereafter described in greater detail with reference to the following examples, although the scope of the present invention is not limited thereto.

Example 1: Identification of New Cancer Antigen Protein by SEREX Method (1) Construction of cDNA Library Total RNA was extracted from a testis tissue of a healthy dog by an Acid guanidium-Phenol-Chloroform method and then a polyA RNA was purified according to protocols included with an Oligotex-dT30 mRNA purification Kit (Takara Shuzo Co., Ltd.).

A canine testis cDNA phage library was synthesized using the thus obtained mRNA (5 μg). The cDNA phage library was constructed using a cDNA Synthesis Kit, a ZAP-cDNA Synthesis Kit, and a ZAP-cDNA GigapackIII Gold Cloning Kit (STRATAGENE) according to protocols included with the kits. The size of the thus constructed cDNA phage library was $1 \times 10^6$ pfu/ml.

(2) Screening of cDNA Library Using Serum

Immunoscreening was performed using the above constructed canine testis cDNA phage library. Specifically, host *Escherichia coli* (XL1-Blue MRF') was infected with the phage on an NZY agarose plate (Φ90×15 mm) so as to obtain approximately 2500 clones. *E. coli* cells were cultured at 42° C. for 3 to 4 hours to form plaques. The plate was covered with a nitrocellulose membrane (Hybond C Extra: GE Healthcare Bio-Science) impregnated with IPTG (isopropyl-β-D-thiogalactoside) at 37° C. for 4 hours, so that the protein was induced, expressed, and then transferred to the membrane. Subsequently, the membrane was taken and then immersed in TBS (10 mM Tris-HCl, 150 mM NaCl, and pH 7.5) containing 0.5% powdered skim milk, followed by overnight shaking at 4° C., thereby suppressing nonspecific reaction. The filter was reacted with a 500-fold diluted serum of a canine patient at room temperature for 2 to 3 hours.

As the above serum of a canine patient, a serum collected from a canine patient with leukemia was used. These sera were stored at −80° C. and then subjected to pre-treatment immediately before use. A method for pretreatment of serum is as follows. Specifically, host *Escherichia coli* (XL1-Blue MRF) was infected with a λ ZAP Express phage in which no foreign gene had been inserted and then cultured overnight on a NZY plate medium at 37° C. Subsequently, buffer (0.2 M NaHCO$_3$ and pH 8.3) containing 0.5 M NaCl was added to the plate, the plate was left to stand at 4° C. for 15 hours, and then a supernatant was collected as an *Escherichia coli*/phage extract. Next, the thus collected *Escherichia coli*/phage extract was applied to an NHS-column (GE Healthcare Bio-Science), so that an *Escherichia coli*.phage-derived protein was immobilized. The serum of a canine patient was applied to the protein-immobilized column for reaction and then an antibody adsorbed to the *Escherichia coli* and phage were removed from the serum. The serum fraction that had passed through the column was diluted 500-fold with TBS containing 0.5% powdered skim milk. The resultant was used as an immunoscreening material.

The above membrane onto which the treated serum and the protein had been blotted was washed 4 times with TBS-T (0.05% Tween20/TBS) and then caused to react with goat anti-dog IgG (Goat anti-Dog IgG-h+L HRP conjugated (BETHYL Laboratories)) diluted 5000-fold with TBS containing 0.5% powdered skim milk as a secondary antibody for 1 hour at room temperature. Detection was performed via an enzyme coloring reaction using an NBT/BCIP reaction solution (Roche). Colonies that matched sites positive for a coloring reaction were collected from the NZY agarose plate (Φ90×15 mm) and then lysed in 500 μl of an SM buffer (100 mM NaCl, 10 mM MgClSO$_4$, 50 mM Tris-HCl, 0.01% gelatin, and pH 7.5). Until colonies positive for coloring reaction were unified, secondary screening and tertiary screening were repeated so that approximately 10,000 phage clones reacting with serum IgG were screened for by a method similar to the above. Thus, 1 positive clone was isolated.

(3) Homology Search for Isolated Antigen Gene

For nucleotide sequence analysis of the 1 positive clone isolated by the above method, a procedure for conversion from phage vectors to plasmid vectors was performed. Specifically, 200 μl of a solution was prepared to contain host *Escherichia coli* (XL1-Blue MRF) so that absorbance OD$_{600}$ was 1.0. The solution was mixed with 100 μl of a purified phage solution and then with 1 μl of an ExAssist helper phage (STRATAGENE), followed by 15 minutes of reaction at 37° C. Three (3) ml of LB medium was added and then culture was performed at 37° C. for 2.5 to 3 hours. Immediately after culture, the temperature of the solution was kept at 70° C. by water bath for 20 minutes, centrifugation was performed at 4° C. and 1000×g for 15 minutes, and then the supernatant was collected as a phagemid solution. Subsequently, 200 μl of a solution was prepared to contain phagemid host *Escherichia coli* (SOLR) so that absorbance OD$_{600}$ was 1.0. The solution was mixed with 10 μl of a purified phage solution, followed by 15 minutes of reaction at 37° C. The solution (50 μl) was seeded on LB agar medium containing ampicillin (final concentration of 50 μg/ml) and then cultured overnight at 37° C. Transformed SOLR single colony was collected and then cultured in LB medium containing ampicillin (final concentration: 50 μg/ml) at 37° C. A plasmid DNA containing the insert of interest was purified using a QIAGEN plasmid Miniprep Kit (QIAGEN).

The purified plasmid was subjected to analysis of the full-length insert sequence by a primer walking method using the T3 primer of SEQ ID NO: 17 and the T7 primer of SEQ ID NO: 18. As a result of sequence analysis, the gene sequence of SEQ ID NO: 3 was obtained. A sequence identity search program, BLAST search (http://www.ncbi.nlm.nih.gov/BLAST/), was performed using the nucleotide sequence of the genes and the amino acid sequence thereof. As a result of this sequence identity search with known genes, it was revealed that the obtained gene was MCEMP1 gene. The sequence identity with human MCEMP1, a human homolog of canine MCEMP1, was 70% in terms of nucleotide sequence and 51% in terms of amino acid sequence. The sequence identity with feline MCEMP1 was 83% in terms of nucleotide sequence and 64% in terms of amino acid sequence. The sequence identity with mouse MCEMP1, a mouse homolog of canine MCEMP1, was 65% in terms of nucleotide sequence and 47% in terms of amino acid sequence. The nucleotide sequence of human MCEMP1 is shown in SEQ ID NO: 1 and the amino acid sequence of the same is shown in SEQ ID NO: 2. The nucleotide sequence of feline MCEMP1 is shown in SEQ ID NO: 5 and the amino acid sequence of the same is shown in SEQ ID NO: 6. The nucleotide sequence of mouse MCEMP1 is shown in SEQ ID NO: 7 and the amino acid sequence of the same is shown in SEQ ID NO: 8.

(4) Gene Expression Analysis in Each Tissue

Figure 2:
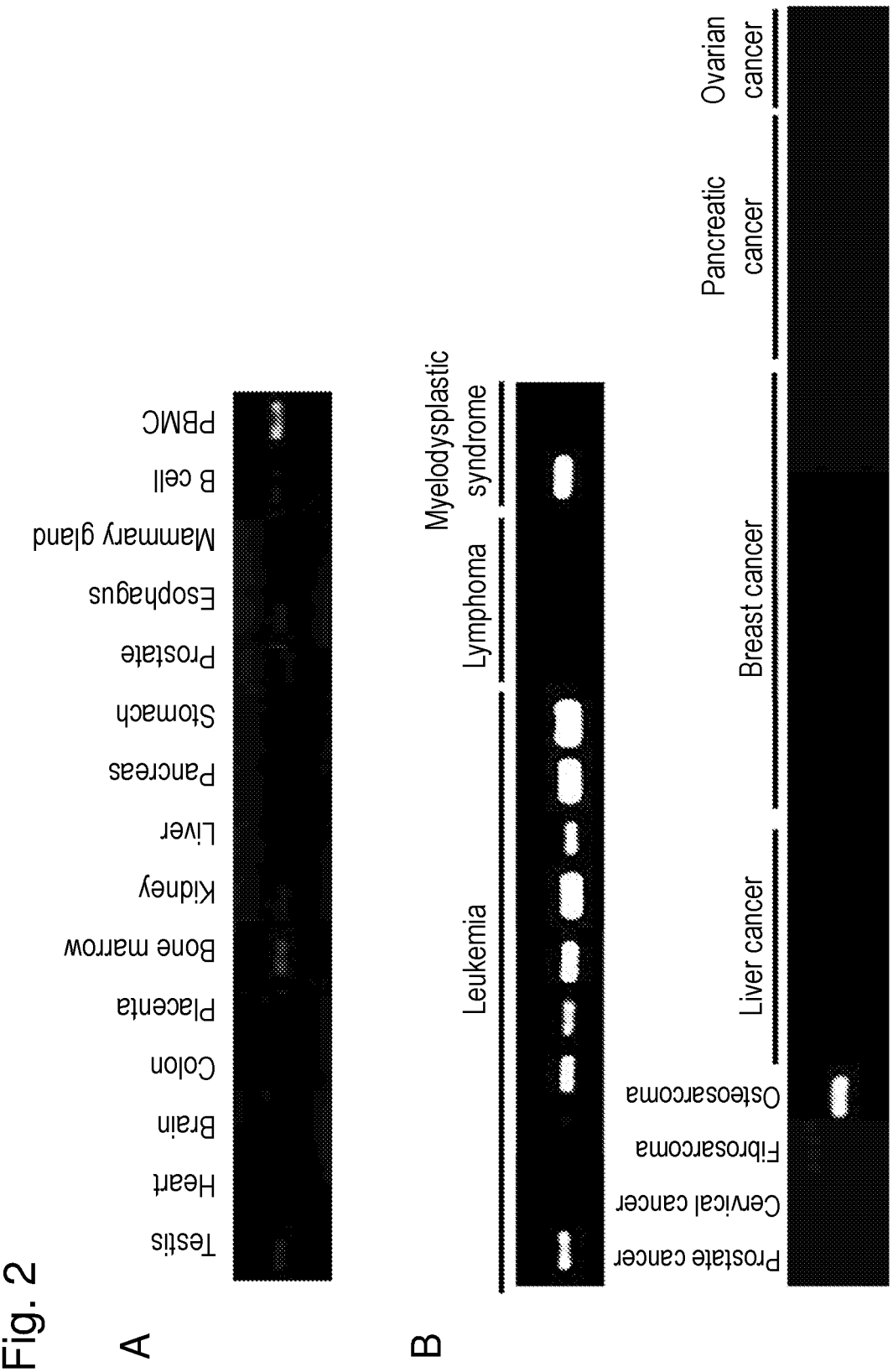
FIG. 2 shows expression patterns of the identified MCEMP1 gene in each of human tissues and cancer cell lines.
Figure 3:
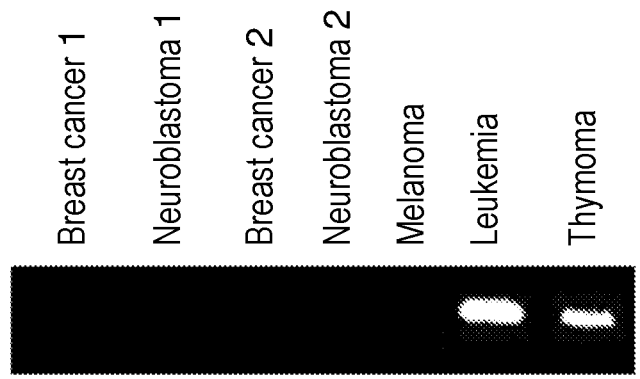
FIG. 3 shows expression patterns of the identified mouse MCEMP1 gene in each of mouse cancer cell lines.

Expression of the gene obtained by the above method in canine, human, and mouse various normal tissues, various tumor tissues, and various cancer cell lines was examined by an RT-PCR (reverse transcription-PCR) method. A reverse transcription reaction was performed as follows. Specifically, total RNA was extracted from each tissue (50 mg to 100 mg) and each cell line (5 to 10×10$^6$ cells) using a TRIZOL reagent (Thermo Fisher Scientific) according to protocols included therewith. cDNA was synthesized using the total RNA and Superscript First-Strand Synthesis System for RT-PCR (Thermo Fisher Scientific) according to protocols included with the kit. Gene Pool cDNA (Thermo Fisher Scientific), QUICK-Clone cDNA (Clontech Laboratories, Inc.), and Large-Insert cDNA Library (Clontech Laboratories, Inc.) were used as cDNAs from human normal tissues (brain, testis, colon, and placenta). PCR was performed as follows using primers specific to the obtained gene (canine primers: SEQ ID NOS: 19 and 20, human primers: SEQ ID NOS: 21 and 22, mouse primers: SEQ ID NOS: 23 and 24). Specifically, PCR was performed by repeating 30 times a cycle of 94° C./30 seconds, 55° C./30 seconds, and 72° C./1 minute using a Thermal Cycler (BIO RAD) and a reaction solution adjusted to a total amount of 25 μl through addition of each reagent and an attached buffer (0.25 μl of the cDNA sample prepared by reverse transcription reaction, the above primers (2 μM each), dNTP (0.2 mM each), and 0.65 U of ExTaq polymerase (Takara Shuzo)). As a result, as shown in FIG. 1, strong expression of the canine MCEMP1 gene was observed in mastocytoma and perianal adenocarcinoma in the case of canine tumor tissues (FIG. 1). Furthermore, expression of the human MCEMP1 gene was not observed in almost all healthy human tissues. On the other hand, strong expression of the human MCEMP1 gene was observed in the cell lines of leukemia, myelodysplastic syndrome, and osteosarcoma, in the case of human cancer cells (FIG. 2). Furthermore, expression of the mouse MCEMP1 gene was detected in the cell lines of leukemia, melanoma, and neuroblastoma (FIG. 3).

Example: 2 Preparation of Human MCEMP1 Protein (1) Cloning of Full-Length cDNA Encoding Human MCEMP1, and cDNA Encoding Extracellular Region of Human MCEMP1

Full-length cDNA encoding human MCEMP1 was cloned by the following method based on the gene of SEQ ID NO:

1 obtained in Example 1. PCR was performed by repeating 30 times a cycle of 98° C./10 seconds, 55° C./15 seconds, and 72° C./1 minute using a Thermal Cycler (BIO RAD) and a reaction solution adjusted to a total amount of 50 μl through addition of each reagent and an attached buffer (1 μl of cDNA (which was from a variety of tissue/cell-derived cDNAs prepared in Example 1 and observed for their expression by RT-PCR), 2 types of primers (0.4 μM each; SEQ ID NOS: 25 and 26) containing EcoRI and NotI restriction enzyme cleavage sequences, 0.2 mM dNTP, 1.25 U PrimeSTAR HS polymerase (Takara Shuzo)). The above 2 types of primers were used to amplify the region encoding the full-length amino acid sequence of SEQ ID NO: 2. After PCR, the thus amplified DNA was subjected to 1% agarose gel electrophoresis and then a DNA fragment of approximately 0.6 kbp was purified using a QIAquick Gel Extraction Kit (QIAGEN). The thus obtained PCR amplification product was inserted into pcDNA3.1 (Thermo Fisher Scientific) (hereinafter, the resultant is referred to as human MCEMP1/pcDNA3.1). The amplification product was also confirmed, by sequencing using a DNA sequencer, to have a cDNA sequence encoding human MCEMP1. The sequence shown in SEQ ID NO: 1 is the nucleotide sequence of the human MCEMP1 gene, and the sequence shown in SEQ ID NO: 2 is the amino acid sequence of the human MCEMP1 protein.

Further, PCR was performed based on SEQ ID NO: 1 by repeating 30 times a cycle of 98° C./10 seconds, 55° C./15 seconds, and 72° C./30 seconds using a Thermal Cycler (BIO RAD) and a reaction solution adjusted to a total amount of 50 μl through addition of each reagent and an attached buffer (2 types of primers (0.4 μM each; SEQ ID NOS: 27 and 28) containing KpnI and EcoRI restriction enzyme cleavage sequences, 0.2 mM dNTP, 1.25 U PrimeSTAR HS polymerase (Takara Shuzo)). The above 2 types of primers were used to amplify the region encoding SEQ ID NO: 10 comprising the amino acid sequence of the extracellular region of the MCEMP1 protein, in SEQ ID NO: 1. After PCR, the thus amplified DNA was subjected to 1% agarose gel electrophoresis and then a DNA fragment of approximately 0.3 kbp was purified using a QIAquick Gel Extraction Kit (QIAGEN). The thus obtained PCR amplification product was ligated to pSecTagB (Thermo Fisher Scientific) having an insert of cDNA encoding the mouse IgG2a Fc protein to prepare an expression vector encoding a human MCEMP1 extracellular region/mouse IgG2a Fc fusion protein (hereinafter, referred to as hMCEMP1ECD-mIgG2aFc) (hereinafter, the obtained expression vector is referred to as pSecB-hMCEMP1ECD-mIgG2aFc). The amplification product was also confirmed, by sequencing using a DNA sequencer, to have a cDNA sequence encoding hMCEMP1ECD-mIgG2aFc. The sequence shown in SEQ ID NO: 29 is the nucleotide sequence encoding hMCEMP1ECD-mIgG2aFc, and the sequence shown in SEQ ID NO: 30 is the amino acid sequence of hMCEMP1ECD-mIgG2aFc.

(2) Preparation of hMCEMP1ECD-mIgG2aFc hMCEMP1ECD-mIgG2aFc was prepared as an immunizing antigen for preparing antibodies to MCEMP1.

The expression vector pSecB-hMCEMP1ECD-mIgG2aFc was introduced by the lipofection method into human embryonic kidney cell line HEK293 cells and purification of hMCEMP1ECD-mIgG2aFc was carried out from a culture supernatant obtained 7 days after introduction. The culture supernatant was applied to a Hi Trap Protein A HP column (GE Healthcare Bio-Science), which was then washed with a binding buffer (20 mM sodium phosphate (pH 7.0)), followed by elution with an elution buffer (0.1 M glycine-HCl (pH 2.7)). Eluates were immediately neutralized by elution into a tube supplemented with a neutralization buffer (1 M Tris-HCl (pH 9.0)). Next, the buffer in the eluates obtained by the above method was replaced with physiological phosphate buffer (Nissui Pharmaceutical Co., Ltd.) using ultrafiltration NANOSEP 10K OMEGA (PALL). Sterilized filtration was performed using 0.22-μm HT Tuffryn Acrodisc (PALL) and then the resultants were used for the Following Experiments.

Example 3: Preparation of Polyclonal Antibody Binding to Extracellular Region of MCEMP1

(1) Preparation of Polyclonal Antibody to MCEMP1

To obtain an antibody binding to the extracellular region of MCEMP1, hMCEMP1ECD-mIgG2aFc (0.1 mg) prepared as described above as an antigen was mixed with a complete Freund's adjuvant (CFA) solution in an amount equivalent thereto. The mixture was subcutaneously administered to a mouse 4 times every 2 weeks. Subsequently, blood was collected, so that an antiserum containing a polyclonal antibody was obtained. Furthermore, the antiserum was purified using a protein G carrier (GE Healthcare Bio-Sciences) and then a polyclonal antibody against hMCEMP1ECD-mIgG2aFc was obtained. In addition, an antibody obtained by purifying serum of mice to which no antigen had been administered with the use of a protein G carrier in the manner described above was designated as a control antibody.

(2) Establishment of Cells Stably Expressing Full-Length Human MCEMP1

Human MCEMP1/pcDNA3.1 prepared as described above was introduced by the lipofection method into CHO-K1 cells (ATCC) and then selection was performed using 500 μg/ml G418 (Nacalai Tesque, Inc.) to establish a CHO cell line stably expressing full-length human MCEMP1 (CHO-human MCEMP1). Cells obtained by introducing an expression vector (hereinafter, referred to as emp/pcDNA3.1) having no insert of cDNA encoding MCEMP1 and then performing selection in the manner described above was designated as control cells (hereinafter, referred to as CHO-emp).

(3) Analysis of Antigen Protein Expression on Cell Surface

Next, it was examined whether or not the polyclonal antibody prepared in (1) above specifically reacted with MCEMP1 expressed on the surfaces of the cells established in (2) above. The CHO-human MCEMP1 cells or the CHO-emp cells ($10^6$ cells each) were centrifuged in a 1.5-ml microcentrifugal tube. The polyclonal antibody against MCEMP1 (2 μg) (5 μl) prepared in (1) above was added thereto. The resultant was further suspended in PBS containing 0.1% fetal bovine serum (95 μl) and then left to stand on ice for 1 hour. After washing with PBS, the resultant was suspended in PBS containing an FITC-labeled goat anti-mouse IgG antibody (Santa Cruz Biotechnology, Inc.) (5 μl) and 0.1% fetal bovine serum (FBS) (95 μl) and then left to stand on ice for 1 hour. After washing with PBS, fluorescence intensity was measured using FACSCalibur (Becton, Dickinson and Company). Meanwhile, a procedure similar to the above was performed using the control antibody prepared in (1) above instead of the polyclonal antibody against MCEMP1, so that a control was prepared. As a result, 208% increase in fluorescence intensity was found in the CHO-human MCEMP1 cells to which the anti-human MCEMP1 antibody had been added, as compared with the control. Meanwhile, a procedure similar to the above was performed for the CHO-emp cells. As a result, 0% increase in fluorescence intensity was found in the CHO-emp cells to which the anti-human MCEMP1 antibody had been added, as compared with the control. Based on the above, it was revealed that the anti-human MCEMP1 antibody was capable of specifically binding to the MCEMP1 protein expressed on the cell membrane surfaces. In addition, the rate of increase in fluorescence intensity is represented by the rate of increase in mean fluorescence intensity (MFI value) in cells. It was calculated by the following equation.

Rate of increase in mean fluorescence intensity(rate of increase in fluorescence intensity)(%)=((MFI value of cells reacted with an anti-human MCEMP1 antibody)−(control MFI value))/(control MFI value)×100

Next, it was examined whether or not the MCEMP1 protein was expressed on cell surfaces of 2 types of leukemia cell lines (U937 and THP-1) and 1 type of myelodysplastic syndrome cell line (MDS92) in which MCEMP1 gene expression had been strongly confirmed. Each human cell line ($10^6$ cells) in which gene expression had been confirmed as described above was centrifuged in a 1.5-ml microcentrifugal tube. The polyclonal antibody against MCEMP1 (2 μg) (5 μl) prepared in (1) above was added thereto. The resultant was further suspended in PBS containing 0.1% fetal bovine serum (95 μl) and then left to stand on ice for 1 hour. After washing with PBS, the resultant was suspended in PBS containing an FITC-labeled goat anti-mouse IgG antibody (Santa Cruz Biotechnology, Inc.) (5 μl) and 0.1% fetal bovine serum (FBS) (95 μl) and then left to stand on ice for 1 hour. After washing with PBS, fluorescence intensity was measured using FACSCalibur (Becton, Dickinson and Company). Meanwhile, a procedure similar to the above was performed using the control antibody prepared in (1) above instead of the polyclonal antibody against MCEMP1, so that a control was prepared. As a result, fluorescence intensity was found to be at least 30% stronger in all cells to which the anti-human MCEMP1 antibody had been added than that in control cells. Specifically, the following increases in fluorescence intensity were confirmed: U937: 175%, THP-1: 123%, and MDS92: 137%. Based on the above, it was confirmed that the MCEMP1 protein was expressed on the cell membrane surfaces of the above human cancer cell lines.

In addition, the rate of increase in fluorescence intensity is represented by the rate of increase in mean fluorescence intensity (MFI value) in cells. It was calculated by the following equation.

Rate of increase in mean fluorescence intensity(rate of increase in fluorescence intensity)(%)=((MFI value of cells reacted with an anti-human MCEMP1 antibody)−(control MFI value))/(control MFI value)×100

Example 4: Antitumor Effects (ADCC Activity) of Polyclonal Antibody Against MCEMP1 to Cancer Cells Next, it was examined whether or not a polyclonal antibody against MCEMP1 would be able to damage MCEMP1-expressing tumor cells. Evaluation was carried out using the polyclonal antibody against human MCEMP1 prepared in Example 3. A human leukemia cell line U937 and a myelodysplastic syndrome cell line MDS92 ($10^6$ cells each), in which MCEMP1 expression had been confirmed, were separately collected into a 50-ml centrifugal tube. Chromium 51 (100 μCi) was added thereto, followed by incubation at 37° C. for 2 hours. Thereafter, cells were washed 3 times with an RPMI1640 medium containing 10% fetal bovine serum and added to wells ($10^3$ cells per well) in 96-well V-bottom plates. The above polyclonal antibody against human MCEMP1 was added thereto (1 μg per well). Further, lymphocytes separated from mouse peripheral blood were added thereto ($2 \times 10^5$ cells per well), followed by culture under conditions of 37° C. and 5% $CO_2$ for 4 hours. After culture, the level of chromium (Cr) 51 released from damaged tumor cells in each culture supernatant was determined. Then, the ADCC activity of the polyclonal antibody against human MCEMP1 to cancer cells was calculated. As a result, ADCC activities against the U937 cells (18.1%) and the MDS92 cells (17.3%) were confirmed (see FIG. 4). Meanwhile, substantially no activity against each cell line was observed in a case in which a procedure similar to the above was performed using the control antibody prepared from peripheral blood of a mouse that had not been immunized with an antigen (Example 3) or in a case in which no antibody was added (see FIG. 4). Accordingly, it was revealed that MCEMP1-expressing tumor cells can be damaged by inducing the ADCC activity with the use of an antibody against MCEMP1.

Figure 4:
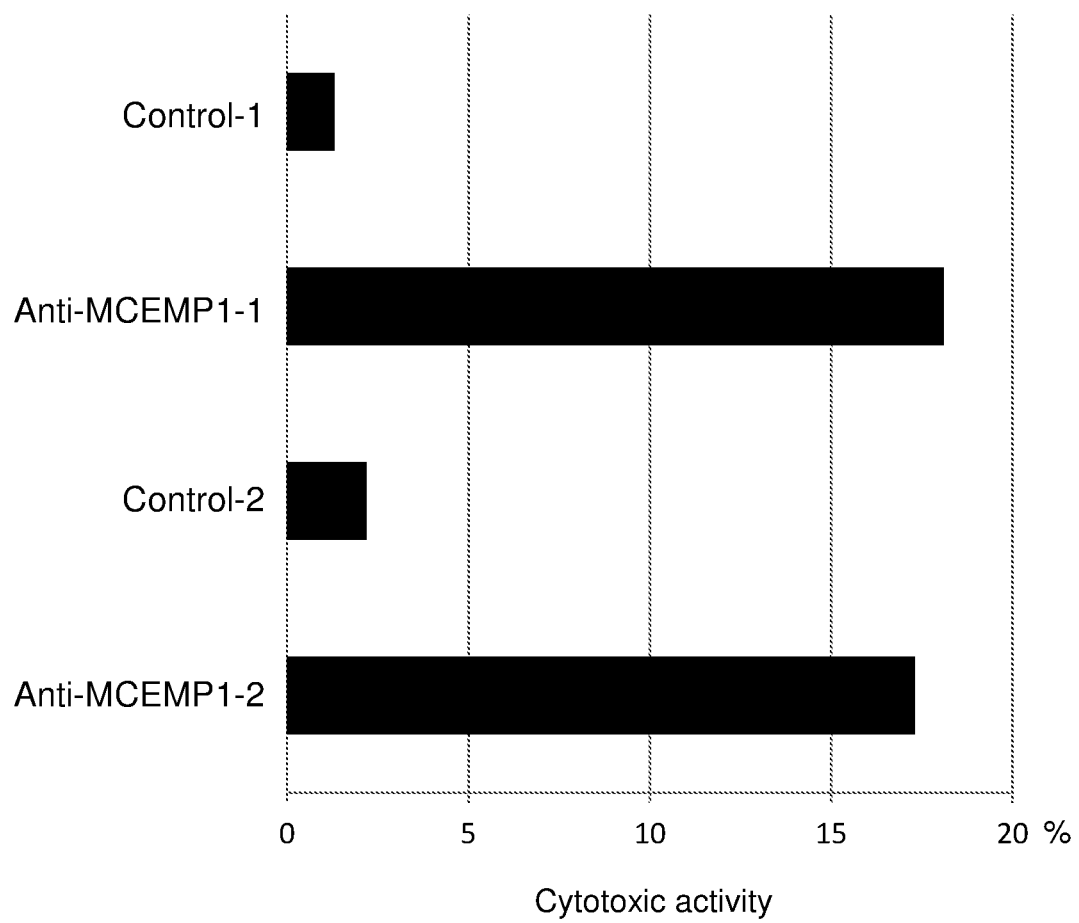
FIG. 4 shows the cytotoxic activity of polyclonal antibodies to MCEMP1 (anti-MCEMP1 polyclonal antibody) against the leukemia cell line (U937) and the myelodysplastic syndrome cell line (MDS92) expressing MCEMP1 gene. In this figure, Control-1 shows the cytotoxic activity against the U937 cells after addition of a control polyclonal antibody, Anti-MCEMP1-1 shows the cytotoxic activity against the U937 cells after addition of the anti-MCEMP1 polyclonal antibody. Control-2 shows the cytotoxic activity against the MDS92 cells after addition of the control polyclonal antibody, MCEMP1-2 shows the cytotoxic activity against the MDS92 cells after addition of the anti-MCEMP1 polyclonal antibody.

In addition, for cytotoxic activity (ADCC activity) in FIG. 4, an antibody against MCEMP1 used in the present invention, mouse lymphocytes, and $10^3$ cells of the above cell lines incorporating chromium 51 were mixed together and cultured for 4 hours, and then the level of chromium 51 released into the medium was determined as described above. Then, the cytotoxic activity to the leukemia cell line was calculated by the following equation*.

*Equation: Cytotoxic activity (%)=[(the level of chromium 51 released from U937 to which an antibody against MCEMP1 and mouse lymphocytes were added)/(the level of chromium 51 released from target cells to which 1N hydrochloric acid was added)]×100

INDUSTRIAL APPLICABILITY

The antibodies of the present invention are useful for treatment and/or prevention of cancers.

All publications, patents, and patent applications cited herein are incorporated herein by reference in their entirety.

The invention claimed is:

1. A method of treating a cancer, said method comprising administering a pharmaceutical composition to a subject in need thereof,
wherein said pharmaceutical composition comprises as an active ingredient, an antibody having an immunological reactivity with a portion of the extracellular region of MCEMP1 protein, wherein the portion consists of the amino acid sequence of SEQ ID NO: 10, and the antibody is conjugated with a cytotoxic agent,
wherein said cancer is a cancer expressing MCEMP1 on the cell surface and said cancer is leukemia or myelodysplastic syndrome.

2. The method according to claim 1, wherein the antibody is a monoclonal or polyclonal antibody.

3. The method according to claim 2, wherein the antibody is a human antibody, a humanized antibody, a chimeric antibody, a single chain antibody, or a multispecific antibody.

4. The method according to claim 1, wherein the antibody is a human antibody, a humanized antibody, a chimeric antibody, a single chain antibody, or a multispecific antibody.

5. The method according to claim 1, further comprising administering a pharmaceutical composition comprising an antitumor agent to the subject.

6. A method for treating a cancer, which comprises administering, to a subject, an antibody having an immunological reactivity with a portion of the extracellular region of MCEMP1 protein, wherein the portion consists of the amino acid sequence of SEQ ID NO: 10, and the antibody is conjugated with a cytotoxic agent,
wherein said cancer is a cancer expressing MCEMP1 on the cell surface and said cancer is leukemia or myelodysplastic syndrome.

7. The method according to claim 6, wherein the antibody is a monoclonal or polyclonal antibody.

8. The method according to claim 6, wherein the antibody is a human antibody, a humanized antibody, a chimeric antibody, a single chain antibody, or a multispecific antibody.

* * * * *